(12) United States Patent
Cirpus et al.

(10) Patent No.: US 7,629,503 B2
(45) Date of Patent: Dec. 8, 2009

(54) Δ-4 DESATURASES FROM *EUGLENA GRACILIS*, EXPRESSING PLANTS, AND OILS CONTAINING PUFA

(75) Inventors: Petra Cirpus, Mannheim (DE); Jörg Bauer, Ludwigshafen (DE); Astrid Meyer, Köln (DE); Ernst Heinz, Hamburg (DE); Ulrich Zähringer, Ahrensburg (DE)

(73) Assignee: BASF Plant Science GmbH, Ludwigshafen (DE)

( * ) Notice: Subject to any disclaimer, the term of this patent is extended or adjusted under 35 U.S.C. 154(b) by 291 days.

(21) Appl. No.: 10/552,127

(22) PCT Filed: Apr. 6, 2004

(86) PCT No.: PCT/EP2004/003628

§ 371 (c)(1),
(2), (4) Date: Oct. 5, 2005

(87) PCT Pub. No.: WO2004/090123

PCT Pub. Date: Oct. 21, 2004

(65) Prior Publication Data

US 2006/0218668 A1    Sep. 28, 2006

(30) Foreign Application Priority Data

Apr. 8, 2003    (DE) ................. 103 16 267

(51) Int. Cl.
A01H 5/00  (2006.01)
C12N 15/82 (2006.01)
C07H 21/04 (2006.01)

(52) U.S. Cl. .............. 800/298; 800/281; 435/320.1; 435/252.3; 536/23.2

(58) Field of Classification Search ............. None
See application file for complete search history.

(56) References Cited

U.S. PATENT DOCUMENTS 5,614,393 A    3/1997   Thomas et al.

FOREIGN PATENT DOCUMENTS

| EP | 0 550 162 A1 | 7/1993 |
|---|---|---|
| EP | 0 794 250 A1 | 9/1997 |
| WO | WO-91/13972 | 9/1991 |
| WO | WO-93/06712 | 4/1993 |
| WO | WO-93/11245 | 6/1993 |
| WO | WO-94/11516 | 5/1994 |
| WO | WO-94/18337 | 8/1994 |
| WO | WO-95/18222 | 7/1995 |
| WO | WO-96/21022 | 7/1996 |
| WO | WO-97/21340 | 6/1997 |
| WO | WO-97/30582 | 8/1997 |
| WO | WO-98/46763 | 10/1998 |
| WO | WO-98/46764 | 10/1998 |
| WO | WO-98/46765 | 10/1998 |
| WO | WO-98/46776 | 10/1998 |
| WO | WO-99/27111 | 6/1999 |
| WO | WO-99/64616 | 12/1999 |
| WO | WO-00/21557 | 4/2000 |
| WO | WO-02/26946 | 4/2002 |
| WO | WO-02/090493 | 11/2002 |

OTHER PUBLICATIONS

Barsanti, L. et al., "Fatty Acid Content in Wild Type and WZSL Mutant of *Euglena gracilis*", Journal of Applied Phycology, 2000, vol. 12, pp. 515-520.

Horrocks, L. A. et al., "Health Benefits of Docosahexaenoic Acid (DHA)", Pharmacological Research, 1999, vol. 40, No. 3, pp. 211-225.

Huang, Y. S. et al., "Cloning of Δ12- and Δ6-Desaturases from *Mortierella alpina* and Recombinant Production of γ-Linolenic Acid in *Saccharomyces cerevisiae*", Lipids, 1999, vol. 34, No. 7, pp. 649-659.

Hunter, J. E., "Studies on Effects of Dietary Fatty Acids as Related to Their Position on Triglycerides", Lipids, 2001, vol. 36, No. 7, pp. 655-668.

Alonso, D. L. et al., "Plants as 'chemical factories' for the Production of Polyunsaturated Fatty Acids", Biotechnology Advances, 2000, vol. 18, pp. 481-497.

McKeon, T. et al., "Stearoyl-Acyl Carrier Protein Desaturase from Safflower Seeds", Methods in Enzymology, 1981, vol. 71, pp. 275-281.

Meyer, A. et al., "Biosynthesis of Docosahexaenoic Acid in *Euglena gracilis*: Biochemical and Molecular Evidence for the Involvement of a Δ4-Fatty Acyl Group Desaturase", Biochemistry, 2003, vol. 42, pp. 9779-9788.

(Continued)

*Primary Examiner*—Elizabeth F McElwain
(74) *Attorney, Agent, or Firm*—Connolly Bove Lodge & Hutz LLP

(57) ABSTRACT

The present invention relates to an improved process for the specific preparation of unsaturated ω-3 fatty acids, and to a process for preparing triglycerides having an increased content of unsaturated fatty acids, particularly of ω-3 fatty acids having more than three double bonds. The invention relates to the preparation of a transgenic organism, preferably a transgenic plant or a transgenic microorganism, having increased content of fatty acids, oils or lipids having Δ-4 double bonds owing to the expression of a Δ-4-desaturase from *Euglena gracilis*.

The invention additionally relates to expression cassettes comprising a nucleic acid sequence, a vector and organisms comprising at least one nucleic acid sequence or one expression cassette. The invention additionally relates to unsaturated fatty acids and to triglycerides having an increased content of unsaturated fatty acids and to the use thereof.

Fatty acids and triglycerides have a large number of uses in the food industry, in animal nutrition, cosmetics and in the drugs sector. They are suitable for a wide variety of uses depending on whether they are free saturated or unsaturated fatty acids or triglycerides having an increased content of saturated or unsaturated fatty acids.

13 Claims, 7 Drawing Sheets

OTHER PUBLICATIONS

Pereira, S. L. et al., "Recent Advances in the Study of Fatty Acid Desaturases from Animals and Lower Eukaryotes", Prostaglandins, Leukotrienes and Essential Fatty Acids, 2003, vol. 68, pp. 97-106.

Poulos, A. "Very Long Chain Fatty Acids in Higher Animals—A Review", Lipids, 1995, vol. 30, No. 1, pp. 1-14.

Sakuradani, E. et al., "Δ6-Fatty Acid Desaturase from an Arachidonic Acid-Producing *Mortierella* Fungus. Gene Cloning and its Heterologous Expression in a Fungus, *Aspergillus*", Gene, 1999, vol. 238, pp. 445-453.

Stukey, J. E. et al., "The *OLE1* Gene of *Saccharomyces cerevisiae* Encodes the Δ9 Fatty Acid Desaturase and Can Be Functionally Replaced by the Rat Stearoyl-CoA Desaturase Gene", The Journal of Biological Chemistry, 1990, vol. 265, No. 33, pp. 20144-20149.

Voss, A. et al., "The Metabolism of 7, 10, 13, 16, 19-Docosapentaenoic Acid to 4, 7, 10, 13, 16, 19-Docosahexaenoic Acid in Rat Liver is Independent of a 4-Desaturase", The Journal of Biological Chemistry, 1991, vol. 266, No. 30, pp. 19995-20000.

Wada, H. et al., "Enhancement of Chilling Tolerance of a Cyanobacterium by Genetic Manipulation of Fatty Acid Desaturation", Nature, 1990, vol. 347, pp. 200-203.

Wallis, J. G. et al., "The Δ8-Desaturase of *Euglena gracilis*: An Alternate Pathway for Synthesis of 20-Carbon Polyunsaturated Fatty Acids", Archives of Biochemistry and Biophysics, 1999, vol. 365, No. 2, pp. 307-316.

Wang, X. et al., "Biosynthesis and Regulation of Linolenic Acid in Higher Plants", Plant Physiol. Biochem., 1988, vol. 26, No. 6, pp. 777-792.

Yu, R. et al., "Production of Eicosapentaenoic Acid by a Recombinant Marine Cyanobacterium, *Synechococcus* sp.", Lipids, 2000, vol. 35, No. 10, pp. 1061-1064.

Zank, T. K. et al., "Cloning and Functional Characterisation of an Enzyme Involved in the Elongation of Δ6-Polyunsaturated Fatty Acids from the Moss *Physcomitrella patens*", The Plant Journal, 2002, vol. 31, No. 3, pp. 255-268.

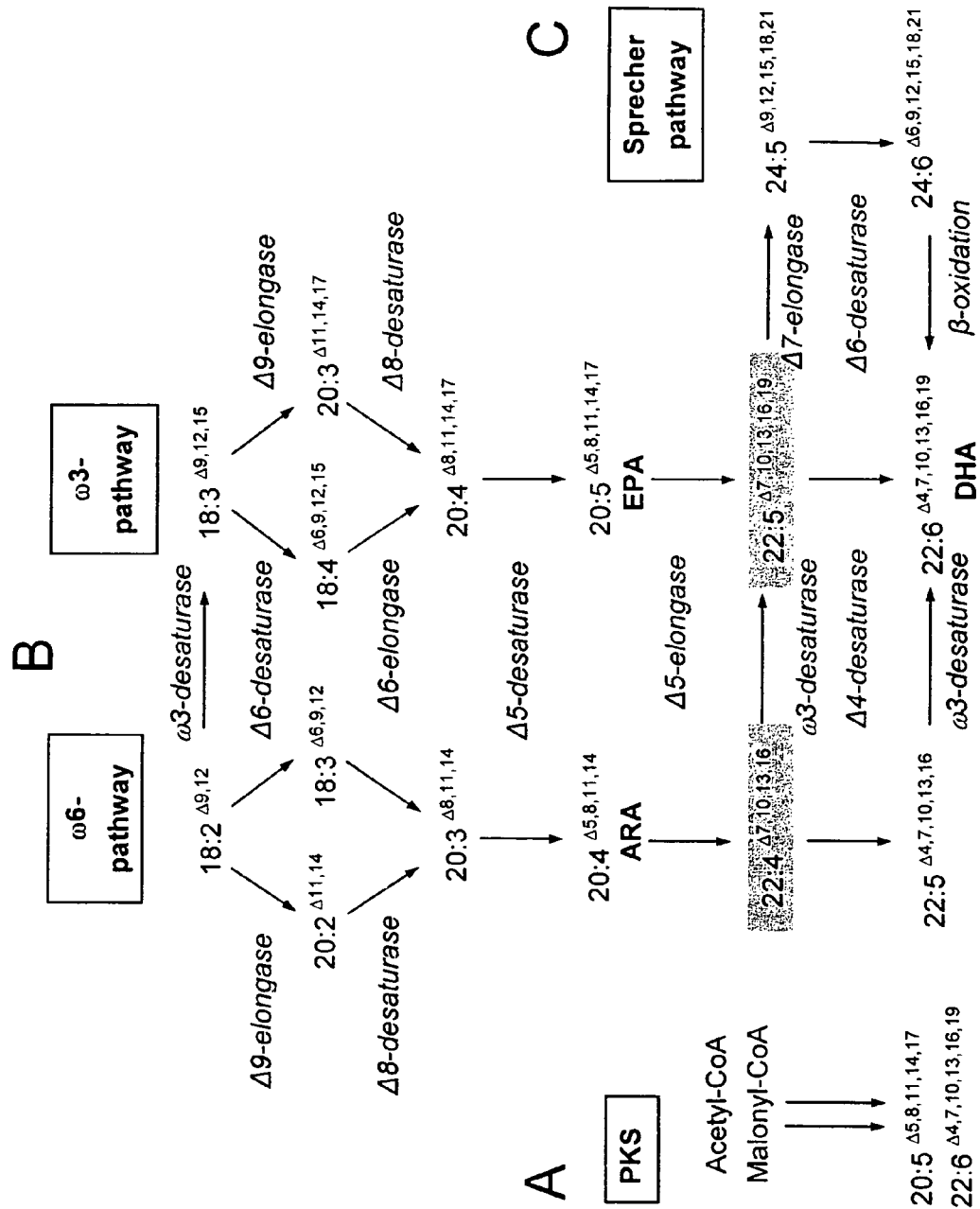
Figure 1: Various synthetic pathways for the biosynthesis of DHA (docosahexaenoic acid)

Figure 2: Sequence comparison of the Δ4-desaturases from Euglena gracilis and Thraustochytrium (WO 200226946). The two sequences show 35% identity [CLUSTAL W(1.60) multiple sequence alignment]

```
Euglena    MLVLFGNFYVKQYSQKNGKPENGATPENGAKPQPCENGTVEKRENDTANVRPTRPAGPPP
Thrausto   ------------------------------------------------------------

Euglena    ATYYDSLAVSGQGKERLFTTDEVRRHILPTDGWLTCHEGVYDVTDFLAKHPGGVITLGL
Thrausto   --------MTVGYDEEIPFEQVRAHNKPDDAWCAIHGHVYDVTKFASVHPGGDILLAA Euglena    GRDCTILIESYHPAGRPDKVMEKYRIGTLQDP---------------KTFYAWGESDFY
Thrausto   GKEATVLYETYHVRGVSDAVLRKYRIGKLPDGQGGANEKEKRTLSGLSSASYYTWNSDFY Euglena    PELKRRALARLKEAGQARRG--GLGVKALLVLTLFFVSWYMWVAHKS----FLWAAVWGF
Thrausto   RVMRERVVARLKERGKARRGGYELWIKAFLLLVGFWSSLYWMCTLDPSFGAILAAMSLGV Euglena    AGSHVGLSIQHDGNHGAFSRNTLVNRLAGWGMDLIGASSTVWEYQHVIGHHQYTNLVS--
Thrausto   FAAFVGTCIQHDGNHGAFAQSRWVNKVAGWTLDMIGASGMTWEFQHVLGHHPYTNLIEEE Euglena    ---------DTLFSLPENDPDVFSSYPLMRMHPDTAWQPHHRFQHLFAFPLFALMTIS
Thrausto   NGLQKVSGKKMDTKLADQESDPDVFSTYPMMRLHPMHQKRWYHRFQHIYGPFIFGFMTIN Euglena    KVLTSDFAVCLSMKKGSIDCSSRLVPLEGQLLFWGAKLANFLLQIVLPCYLHGTAMGLAL
Thrausto   KVVTQDVGVVLRKRLFQIDAECRYASPMYVARFWIMKALTVLYMVALPCYMQGPWHGLKL Euglena    FSVAHLVSGEYLAICFIINHISESCEFMN---------TSFQTAARRTEMLQAAHQA
Thrausto   FAIAHFTCGEVLATMFIVNHIIEGVSYASKDAVKGTMAPPKTMHGVTPMNNTRKEVEAEA Euglena    AEAKKVKPTPPPNDWAVTQVQCCVNWRSGGVLANHLSGGLNHQIEHHLFPSISHANYPTI
Thrausto   SKSGAVVKSVPLDDWAVVQCQTSVNMSVGSWFWNHFSGGLNHQIEHHLFPGLSHETYYHI Euglena    APVVKEVCEEYGLPYKNYVTFWDAVCGMVQHLRLMGAPPVPTNGDKKS-
Thrausto   QDVFQSTCAEYGVPYQHEPSLWTAYWKMLEHLRQLGNEETHESWQRAA-
```

Figure 3: Sequence comparison of the Δ4-desaturases from Euglena gracilis and Thraustochytrium (WO 200226946). GAP alignment GAP Test

| Gap Weight: | 8 | Average Match: | 2.912 | Length Weight: | 2 | Average Mismatch: | -2.003 |
|---|---|---|---|---|---|---|---|
| Quality: | 926 | Length: | 590 | Ratio: | 1.781 | Gaps: | 9 |

Match display thresholds for the alignment(s):
| = IDENTITY;       := 2;       = 1

```
 51  RPTRPAGPPPATYYDSLAVSGQGKERLFTTDEVRRHILPTDGWLTCHEGV  100
       |  :         :|||  |   |     |   |
  1  ............MTVGYDEEIPFEQVRAHNKPDDAWCAIHGHV         31

101  YDVTDFLAKHPGGVITLGLGRDCTILIESYHPAGRPDKVMEKYRIGTLQ  150
     ||||  ||||  ::| :||  |:: |:|:|.||    |: |||||  |
 32  YDVTKFASVHPGGDIILLAAGKEATVLYETYHVRGVSDAVLRKYRIGKLP   81

151  DPK...............TFYAWGESDFYPELKRRALARLKEAGQARR   183
     |.|                .:|  |||  ::  ||||| .||||| .|||

82  DGQGGANEKEKRTLSGLSSASYYTW.NSDFYRVMRERVVARLKERGKARR  130
                                  |:  |||||  |||||  |||

184  GG..LGVKALLVLTLFFVSWY.MWVAHKSF...LWAAVWGFAGSHVGLSI  227
     ||   |  :|||  ||||  |.|     ||      ||
```

Figure 3 continued

```
131 GGYELWIKAFLLLVGFWSSLYMCTLDPSFGAILAAMSLGVFAAFVGTCI 180
            ||||||||||||||||||||||||||||||||||||||||||||||||
228 QHDGNHGAFSRNTLVNRLAGWGMDLIGASSTVWEYQHVIGHHQYTNLVS. 276
    |||||||:... ||::.||| ::.||| ||:.:||:.||| |||:
181 QHDGNHGAFAQSRWVNKVAGWTLDMIGASGMTWEFQHVLGHHPYTNLIEE 230

277 ........DTLFSLPENDPDVFSSYPLMRMHPDTAWQPHHRFQHLF 314
            ||  . |.||||.||:.||:.||  . :|||||::
231 ENGLQKVSGKKMDTKLADQESDPDVFSTYPMMRLHPWHQKRWYHRFQHIY 280

315 APPLFALMTISKVLTSDFAVCLSMKKGSIDCSSRLVPLEGQLLFWGAKLA 364
    :|  |||.||.|. |   |: ||    |   ||
281 GPFIFGFMTINKVVTQDVGVVLRKRLFQIDAECRYASPMYVARFWIMKAL 330

365 NFLLQIVLPCYLHGTAMGLALFSVAHLVSGEYLAICFIINHISESCEFMN 414
    |  :  ||||::  | ||::.|| ||:|||  |:  ||||  |
331 TVLYMVALPCYMQGPWHGLKLFAIAHFTCGEVLATMFIVNHIIEGVSYAS 380

415 TSF........QTAARRTEMLQAAHQA.AEAKK...VKPTPPPNDWAVTQ 452
    |.|           |||      |.|   |  |  . | .||||
381 KDAVKGTMAPPKTMHGVTPMNNTRKEVEAEASKSGAVVKSVPLDDWAVVQ 430

453 VQCCVNWRSGGVLANHLSGGLNHQIEHHLFPSISHANYPTIAPVVKEVCE 502
    | |||  | ||||||||||||||||||||||:||  | |  | .|
431 CQTSVNWSVGSWFWNHFSGGLNHQIEHHLFPGLSHETYYHIQDVFQSTCA 480
```

Figure 3 continued

```
503 EYGLPYKNYVTFWDAVCGMVQHLRLMGAPPVFTNGDKKS*  542
    ||| || |    |   |  | ::||| :|      .  .|
481 EYGVPYQHEPSLWTAYWKMLEHLRQLGNEETHESWQRAA*  520
```

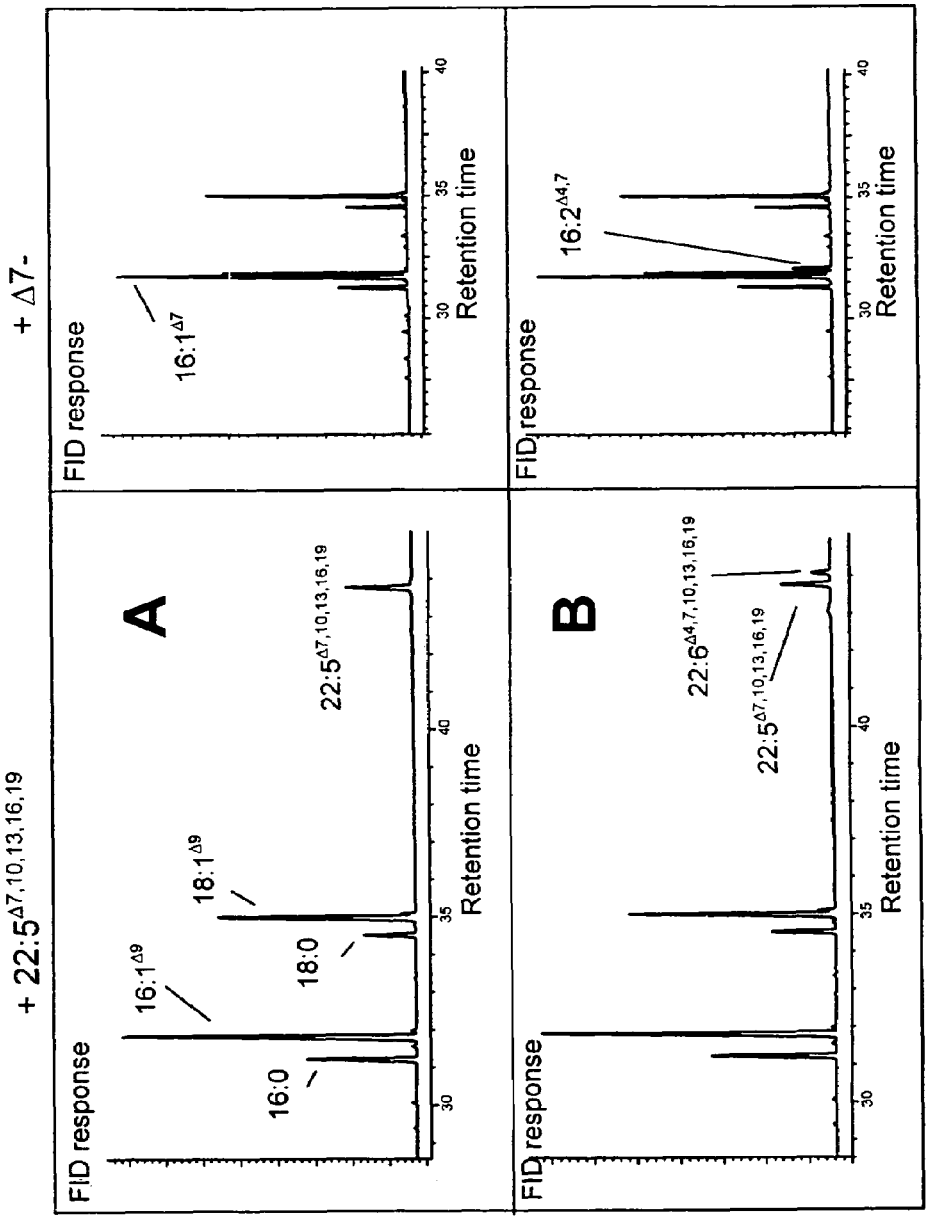
Figure 4: GC analyses of yeast cells fed with DPA (docosapentaenoic acid). Control: yeast cells without Δ4-desaturase [A], conversion to DHA in cells having the Δ4-desaturase (pYES-EGD4-2) [B]

Figure 5: Position analysis of Δ4-desaturated fatty acids. 16:1 Δ7 and 22:4 Δ7,10,13,16 were used for feeding. Conversion is stated in percent.

| acyl group | sn-1 | sn-2 |
|---|---|---|
| 16:0 | 4.9 | 4.2 |
| 16:1 | 31.3 | 21.7 |
| 16:1$^{Δ9}$ | 6.5 | 3.5 |
| 16:2  x 4 | 0.6 | 5.3 |
| 18:0 | 3.6 | 3.3 |
| 18:1$^{Δ9}$ | 2.5 | 11.0 |
| 18:1$^{Δ11}$ | 0.6 | 1.1 |

| acyl group | sn-1 | sn-2 |
|---|---|---|
| 16:0 | 7 | 0.3 |
| 16:1$^{Δ9}$ | 24.2 | 22.2 |
| 18:0 | 3.5 | 0 |
| 18:1$^{Δ9}$ | 12.2 | 23.8 |
| 18:1$^{Δ11}$ | 0.8 | 0.7 |
| 22:4  x 10 | 2.2 | 0.5 |
| 22:5  x 10 | 0.1 | 2.4 |

SEQUENCE LISTING

```
<160> NUMBER OF SEQ ID NOS: 7

<210> SEQ ID NO 1
<211> LENGTH: 1626
<212> TYPE: DNA
<213> ORGANISM: Euglena gracilis
<220> FEATURE:
<221> NAME/KEY: CDS
<222> LOCATION: (1)..(1623)
<223> OTHER INFORMATION: Delta-4-Desaturase

<400> SEQUENCE: 1 atg ttg gtg ctg ttt ggc aat ttc tat gtc aag caa tac tcc caa aag      48
Met Leu Val Leu Phe Gly Asn Phe Tyr Val Lys Gln Tyr Ser Gln Lys
1               5                   10                  15 aac ggc aag ccg gag aac gga gcc acc cct gag aac gga gcg aag ccg      96
Asn Gly Lys Pro Glu Asn Gly Ala Thr Pro Glu Asn Gly Ala Lys Pro
            20                  25                  30 caa cct tgc gag aac ggc acg gtg gaa aag cga gag aat gac acc gcc     144
Gln Pro Cys Glu Asn Gly Thr Val Glu Lys Arg Glu Asn Asp Thr Ala
        35                  40                  45 aac gtt cgg ccc acc cgt cca gct gga ccc ccg ccg gcc acg tac tac     192
Asn Val Arg Pro Thr Arg Pro Ala Gly Pro Pro Pro Ala Thr Tyr Tyr
    50                  55                  60 gac tcc ctg gca gtg tcg ggg cag ggc aag gag cgg ctg ttc acc acc     240
Asp Ser Leu Ala Val Ser Gly Gln Gly Lys Glu Arg Leu Phe Thr Thr
65                  70                  75                  80 gat gag gtg agg cgg cac atc ctc ccc acc gat ggc tgg ctg acg tgc     288
Asp Glu Val Arg Arg His Ile Leu Pro Thr Asp Gly Trp Leu Thr Cys
                85                  90                  95 cac gaa gga gtc tac gat gtc act gat ttc ctt gcc aag cac cct ggt     336
His Glu Gly Val Tyr Asp Val Thr Asp Phe Leu Ala Lys His Pro Gly
            100                 105                 110 ggc ggt gtc atc acg ctg ggc ctt gga agg gac tgc aca atc ctc atc     384
Gly Gly Val Ile Thr Leu Gly Leu Gly Arg Asp Cys Thr Ile Leu Ile
        115                 120                 125 gag tca tac cac cct gct ggg cgc ccg gac aag gtg atg gag aag tac     432
Glu Ser Tyr His Pro Ala Gly Arg Pro Asp Lys Val Met Glu Lys Tyr
    130                 135                 140 cgc att ggt acg ctg cag gac ccc aag acg ttc tat gct tgg gga gag     480
Arg Ile Gly Thr Leu Gln Asp Pro Lys Thr Phe Tyr Ala Trp Gly Glu
145                 150                 155                 160 tcc gat ttc tac cct gag ttg aag cgc cgg gcc ctt gca agg ctg aag     528
Ser Asp Phe Tyr Pro Glu Leu Lys Arg Arg Ala Leu Ala Arg Leu Lys
                165                 170                 175 gag gct ggt cag gcg cgg cgc ggc ggc ctt ggg gtg aag gcc ctc ctg     576
Glu Ala Gly Gln Ala Arg Arg Gly Gly Leu Gly Val Lys Ala Leu Leu
            180                 185                 190
```

```
gtg ctc acc ctc ttc ttc gtg tcg tgg tac atg tgg gtg gcc cac aag      624
Val Leu Thr Leu Phe Phe Val Ser Trp Tyr Met Trp Val Ala His Lys
            195                 200                 205 tcc ttc ctc tgg gcc gcc gtc tgg ggc ttc gcc ggc tcc cac gtc ggg      672
Ser Phe Leu Trp Ala Ala Val Trp Gly Phe Ala Gly Ser His Val Gly
        210                 215                 220 ctg agc atc cag cac gat ggc aac cac ggc gcg ttc agc cgc aac aca      720
Leu Ser Ile Gln His Asp Gly Asn His Gly Ala Phe Ser Arg Asn Thr
225                 230                 235                 240 ctg gtg aac cgc ctg gcg ggg tgg ggc atg gac ttg atc ggc gcg tcg      768
Leu Val Asn Arg Leu Ala Gly Trp Gly Met Asp Leu Ile Gly Ala Ser
            245                 250                 255 tcc acg gtg tgg gag tac cag cac gtc atc ggc cac cac cag tac acc      816
Ser Thr Val Trp Glu Tyr Gln His Val Ile Gly His His Gln Tyr Thr
        260                 265                 270 aac ctc gtg tcg gac acg cta ttc agt ctg cct gag aac gat ccg gac      864
Asn Leu Val Ser Asp Thr Leu Phe Ser Leu Pro Glu Asn Asp Pro Asp
275                 280                 285 gtc ttc tcc agc tac ccg ctg atg cgc atg cac ccg gat acg gcg tgg      912
Val Phe Ser Ser Tyr Pro Leu Met Arg Met His Pro Asp Thr Ala Trp
            290                 295                 300 cag ccg cac cac cgc ttc cag cac ctg ttc gcg ttc cca ctg ttc gcc      960
Gln Pro His His Arg Phe Gln His Leu Phe Ala Phe Pro Leu Phe Ala
305                 310                 315                 320 ctg atg aca atc agc aag gtg ctg acc agc gat ttc gct gtc tgc ctc     1008
Leu Met Thr Ile Ser Lys Val Leu Thr Ser Asp Phe Ala Val Cys Leu
            325                 330                 335 agc atg aag aag ggg tcc atc gac tgc tcc tcc agg ctc gtc cca ctg     1056
Ser Met Lys Lys Gly Ser Ile Asp Cys Ser Ser Arg Leu Val Pro Leu
        340                 345                 350 gag ggg cag ctg ctg ttc tgg ggg gcc aag ctg gcg aac ttc ctg ttg     1104
Glu Gly Gln Leu Leu Phe Trp Gly Ala Lys Leu Ala Asn Phe Leu Leu
355                 360                 365 cag att gtg ttg cca tgc tac ctc cac ggg aca gct atg ggc ctg gcc     1152
Gln Ile Val Leu Pro Cys Tyr Leu His Gly Thr Ala Met Gly Leu Ala
            370                 375                 380 ctc ttc tct gtt gct cac ctt gtg tcg ggg gag tac ctc gcg atc tgc     1200
Leu Phe Ser Val Ala His Leu Val Ser Gly Glu Tyr Leu Ala Ile Cys
385                 390                 395                 400 ttc atc atc aac cac atc agc gag tct tgt gag ttt atg aat aca agc     1248
Phe Ile Ile Asn His Ile Ser Glu Ser Cys Glu Phe Met Asn Thr Ser
            405                 410                 415 ttt caa acc gcc gcc cgg agg aca gag atg ctt cag gca gca cat cag     1296
Phe Gln Thr Ala Ala Arg Arg Thr Glu Met Leu Gln Ala Ala His Gln
        420                 425                 430 gca gcg gag gcc aag aag gtg aag ccc acc cct cca ccg aac gat tgg     1344
Ala Ala Glu Ala Lys Lys Val Lys Pro Thr Pro Pro Pro Asn Asp Trp
435                 440                 445 gct gtg aca cag gtc caa tgc tgc gtg aat tgg aga tca ggt ggc gtg     1392
Ala Val Thr Gln Val Gln Cys Cys Val Asn Trp Arg Ser Gly Gly Val
            450                 455                 460 ttg gcc aat cac ctc tct gga ggc ttg aac cac cag atc gag cat cat     1440
Leu Ala Asn His Leu Ser Gly Gly Leu Asn His Gln Ile Glu His His
465                 470                 475                 480 ctg ttc ccc agc atc tcg cat gcc aac tac ccc acc atc gcc cct gtt     1488
Leu Phe Pro Ser Ile Ser His Ala Asn Tyr Pro Thr Ile Ala Pro Val
            485                 490                 495 gtg aag gag gtg tgc gag gag tac ggg ttg ccg tac aag aat tac gtc     1536
Val Lys Glu Val Cys Glu Glu Tyr Gly Leu Pro Tyr Lys Asn Tyr Val
```

-continued

```
             500                 505                 510
acg ttc tgg gat gca gtc tgt ggc atg gtt cag cac ctc cgg ttg atg    1584
Thr Phe Trp Asp Ala Val Cys Gly Met Val Gln His Leu Arg Leu Met
        515                 520                 525 ggt gct cca ccg gtg cca acg aac ggg gac aaa aag tca taa            1626
Gly Ala Pro Pro Val Pro Thr Asn Gly Asp Lys Lys Ser
    530                 535                 540

<210> SEQ ID NO 2
<211> LENGTH: 541
<212> TYPE: PRT
<213> ORGANISM: Euglena gracilis

<400> SEQUENCE: 2

Met Leu Val Leu Phe Gly Asn Phe Tyr Val Lys Gln Tyr Ser Gln Lys
1               5                   10                  15

Asn Gly Lys Pro Glu Asn Gly Ala Thr Pro Glu Asn Gly Ala Lys Pro
            20                  25                  30

Gln Pro Cys Glu Asn Gly Thr Val Glu Lys Arg Glu Asn Asp Thr Ala
        35                  40                  45

Asn Val Arg Pro Thr Arg Pro Ala Gly Pro Pro Ala Thr Tyr Tyr
    50                  55                  60

Asp Ser Leu Ala Val Ser Gly Gln Gly Lys Glu Arg Leu Phe Thr Thr
65                  70                  75                  80

Asp Glu Val Arg Arg His Ile Leu Pro Thr Asp Gly Trp Leu Thr Cys
                85                  90                  95

His Glu Gly Val Tyr Asp Val Thr Asp Phe Leu Ala Lys His Pro Gly
            100                 105                 110

Gly Gly Val Ile Thr Leu Gly Leu Gly Arg Asp Cys Thr Ile Leu Ile
        115                 120                 125

Glu Ser Tyr His Pro Ala Gly Arg Pro Asp Lys Val Met Glu Lys Tyr
    130                 135                 140

Arg Ile Gly Thr Leu Gln Asp Pro Lys Thr Phe Tyr Ala Trp Gly Glu
145                 150                 155                 160

Ser Asp Phe Tyr Pro Glu Leu Lys Arg Arg Ala Leu Ala Arg Leu Lys
                165                 170                 175

Glu Ala Gly Gln Ala Arg Arg Gly Gly Leu Gly Val Lys Ala Leu Leu
            180                 185                 190

Val Leu Thr Leu Phe Phe Val Ser Trp Tyr Met Trp Val Ala His Lys
        195                 200                 205

Ser Phe Leu Trp Ala Ala Val Trp Gly Phe Ala Gly Ser His Val Gly
    210                 215                 220

Leu Ser Ile Gln His Asp Gly Asn His Gly Ala Phe Ser Arg Asn Thr
225                 230                 235                 240

Leu Val Asn Arg Leu Ala Gly Trp Gly Met Asp Leu Ile Gly Ala Ser
                245                 250                 255

Ser Thr Val Trp Glu Tyr Gln His Val Ile Gly His His Gln Tyr Thr
            260                 265                 270

Asn Leu Val Ser Asp Thr Leu Phe Ser Leu Pro Glu Asn Asp Pro Asp
        275                 280                 285

Val Phe Ser Ser Tyr Pro Leu Met Arg Met His Pro Asp Thr Ala Trp
    290                 295                 300

Gln Pro His His Arg Phe Gln His Leu Phe Ala Phe Pro Leu Phe Ala
305                 310                 315                 320

Leu Met Thr Ile Ser Lys Val Leu Thr Ser Asp Phe Ala Val Cys Leu
```

-continued

```
                    325                 330                 335
Ser Met Lys Lys Gly Ser Ile Asp Cys Ser Ser Arg Leu Val Pro Leu
                340                 345                 350

Glu Gly Gln Leu Leu Phe Trp Gly Ala Lys Leu Ala Asn Phe Leu Leu
            355                 360                 365

Gln Ile Val Leu Pro Cys Tyr Leu His Gly Thr Ala Met Gly Leu Ala
        370                 375                 380

Leu Phe Ser Val Ala His Leu Val Ser Gly Glu Tyr Leu Ala Ile Cys
385                 390                 395                 400

Phe Ile Ile Asn His Ile Ser Glu Ser Cys Glu Phe Met Asn Thr Ser
                405                 410                 415

Phe Gln Thr Ala Ala Arg Arg Thr Glu Met Leu Gln Ala Ala His Gln
            420                 425                 430

Ala Ala Glu Ala Lys Lys Val Lys Pro Thr Pro Pro Asn Asp Trp
        435                 440                 445

Ala Val Thr Gln Val Gln Cys Cys Val Asn Trp Arg Ser Gly Gly Val
        450                 455                 460

Leu Ala Asn His Leu Ser Gly Gly Leu Asn His Gln Ile Glu His His
465                 470                 475                 480

Leu Phe Pro Ser Ile Ser His Ala Asn Tyr Pro Thr Ile Ala Pro Val
                485                 490                 495

Val Lys Glu Val Cys Glu Glu Tyr Gly Leu Pro Tyr Lys Asn Tyr Val
            500                 505                 510

Thr Phe Trp Asp Ala Val Cys Gly Met Val Gln His Leu Arg Leu Met
        515                 520                 525

Gly Ala Pro Pro Val Pro Thr Asn Gly Asp Lys Lys Ser
        530                 535                 540

<210> SEQ ID NO 3
<211> LENGTH: 26
<212> TYPE: DNA
<213> ORGANISM: Unknown
<220> FEATURE:
<221> NAME/KEY: misc_feature
<222> LOCATION: (1)..(26)
<223> OTHER INFORMATION: Forward primer for cloning the shorter reading
      frame (SEQ ID NO: 1) into the vector pYES2

<400> SEQUENCE: 3
ggtaccatgt tggtgctgtt tggcaa                                          26

<210> SEQ ID NO 4
<211> LENGTH: 25
<212> TYPE: DNA
<213> ORGANISM: Unknown
<220> FEATURE:
<221> NAME/KEY: misc_feature
<222> LOCATION: (1)..(25)
<223> OTHER INFORMATION: Reverse primer for cloning the shorter reading
      frame (SEQ ID NO: 1) into the vector pYES2

<400> SEQUENCE: 4
ctcgagttat gactttttgt ccccg                                           25

<210> SEQ ID NO 5
<211> LENGTH: 28
<212> TYPE: DNA
<213> ORGANISM: Unknown
<220> FEATURE:
<221> NAME/KEY: misc_feature
<222> LOCATION: (1)..(28)
```

-continued

```
<223> OTHER INFORMATION: Forward primer for introducing NotI cleavage
      sites at the 5' end of the coding sequence

<400> SEQUENCE: 5
gcggccgcat gttggtgctg tttggcaa                                           28

<210> SEQ ID NO 6
<211> LENGTH: 25
<212> TYPE: DNA
<213> ORGANISM: Unknown
<220> FEATURE:
<221> NAME/KEY: misc_feature
<222> LOCATION: (1)..(25)
<223> OTHER INFORMATION: Reverse primer for introducing NotI cleavage
      sites at the 3' end of the coding sequence

<400> SEQUENCE: 6
gcggccgcat gactttttgt ccccg                                              25

<210> SEQ ID NO 7
<211> LENGTH: 60
<212> TYPE: DNA
<213> ORGANISM: Unknown
<220> FEATURE:
<221> NAME/KEY: misc_feature
<222> LOCATION: (1)..(60)
<223> OTHER INFORMATION: synthesized primer

<400> SEQUENCE: 7
gtcgacccgc ggactagtgg gccctctaga cccgggggat ccggatctgc tggctatgaa       60
```

Δ-4 DESATURASES FROM *EUGLENA GRACILIS*, EXPRESSING PLANTS, AND OILS CONTAINING PUFA

RELATED APPLICATIONS

This application is a national stage application (under 35 U.S.C. 371) of PCT/EP2004/003628 filed Apr. 6, 2004 which claims benefit to German application 103 16 267.4 filed Apr. 8, 2003.

The present invention relates to an improved process for the specific preparation of unsaturated ω-3 fatty acids, and to a process for preparing triglycerides having an increased content of unsaturated fatty acids, particularly of ω-3 fatty acids having more than three double bonds. The invention relates to the preparation of a transgenic organism, preferably a transgenic plant or a transgenic microorganism, having increased content of fatty acids, oils or lipids having Δ-4 double bonds owing to the expression of a Δ-4-desaturase from *Euglena gracilis*.

The invention additionally relates to expression cassettes comprising a nucleic acid sequence, a vector and organisms comprising at least one nucleic acid sequence or one expression cassette. The invention additionally relates to unsaturated fatty acids and to triglycerides having an increased content of unsaturated fatty acids and to the use thereof.

Fatty acids and triglycerides have a large number of uses in the food industry, in animal nutrition, cosmetics and in the drugs sector. They are suitable for a wide variety of uses depending on whether they are free saturated or unsaturated fatty acids or triglycerides having an increased content of saturated or unsaturated fatty acids.

Polyunsaturated long-chain ω-3-fatty acids such as eicosapentaenoic acid (EPA) or docosahexaenoic acid (DPA) are important components of the human diet owing to their various roles in health which comprise aspects such as the development of the brain in children, the functionality of the eye, the synthesis of hormones and other signal substances, and the prevention of cardiovascular complaints, cancer and diabetes (Poulos, A Lipids 30:1-14, 1995; Horrocks, L A and Yeo Y K Pharmacol Res 40:211-225, 1999). There is for this reason a demand for the production of polyunsaturated long-chain fatty acids.

Thus, for example, polyunsaturated fatty acids are added to infant food for increasing the nutritional value, and for unimpeded development of the infant. The various fatty acids and triglycerides are mainly obtained from microorganisms such as *Mortierella* or from oil-producing plants such as soybean, oilseed rape, sunflower and others, in which cases they usually result in the form of their triacylglycerides. However, no long-chain unsaturated fatty acids occur in higher plants. The long-chain fatty acids are derived mostly from fish oil and from the fermentation of appropriate algae (e.g. *Thraustochytrium*) or fungi (e.g. *Mortierella*). The free fatty acids are advantageously prepared by hydrolysis.

Oil having saturated or unsaturated fatty acids are preferred, depending on the purpose of use, and thus, for example, lipids having unsaturated fatty acids, specifically polyunsaturated fatty acids, are preferred in the human diet because they have a beneficial effect on the cholesterol level in the blood and thus on the possibility of heart disease. They are used in various dietetic foods or medicaments.

Because of their beneficial properties, there has in the past been no lack of attempts at making available genes involved in the synthesis of fatty acids or triglycerides for producing oils in various organisms having altered content of unsaturated fatty acids. Thus, WO 91/13972 and its US equivalent describe a Δ-9-desaturase. WO 93/11245 claims a delta-15-desaturase and WO 94/11516 claims a Δ-12-desaturase. Further desaturases are described for example in EP-A-0 550 162, WO 94/18337, WO 97/30582, WO 97/21340, WO 95/18222, EP-Z-0 794 250, Stukey et al., J. Biol. Chem., 265, 1990: 20144-20149, Wada et al., Nature 347, 1990: 200-203 or Huang et al., Lipids 34, 1999: 649-659. The biochemical characterization of the various desaturases has, however, to date been only inadequate because the enzymes can, as membrane-bound proteins, be isolated and characterized only with great difficulty (McKeon et al., Methods in Enzymol. 71, 1981: 12141-12147, Wang et al., Plant Physiol. Biochem., 26, 1988: 777-792). Membrane-bound desaturases are usually characterized by introduction into a suitable organism which is subsequently investigated for enzymic activity through precursor and product analysis. Δ-6-Desaturases are described in WO 93/06712, U.S. Pat. No. 5,614,393, U.S. Pat. No. 5,614, 393, WO 96/21022, WO 0021557 and WO 99/27111, and also the use for production in transgenic organisms is described as in WO 9846763, WO 9846764, WO 9846765. Also described and claimed in this connection is the expression of various desaturases, as in WO 9964616 or WO 9846776 and formation of polyunsaturated fatty acids.

Various synthetic routes are suggested for the synthesis of docosahexaenoic acid (DHA) (FIG. 1). Thus, DHA is produced in marine bacteria such as *Vibrio* sp. or *Shewanella* sp. by the polyketide route (Yu, R. et al. Lipids 35:1061-1064, 2000; Takeyama, H. et al. Microbiology 143:2725-2731, 1197)).

An alternative strategy proceeds via the alternating activity of desaturases and elongases (Zank, T. K. et al. Plant Journal 31:255-268, 2002; Sakuradani, E. et al. Gene 238:445-453, 1999). The last step in this case is the introduction of the double bond in the C4-C5 position by a Δ4-desaturase. It has been demonstrated in this connection by Sprecher et al. (Voss, A. et al. Journal of Biological Chemistry 266:19995-20000, 1991) that DHA can also be synthesized independently of a Δ-4-desaturase in rat livers. However, the so called Sprecher synthetic route (see FIG. 1) is unsuitable for production in plants and microorganisms, because the regulatory mechanisms underlying the α-oxidation are unknown.

Various Δ4-desaturases have been described in WO 200226946 and WO 2002090493.

Concerning the efficiency of expression of desaturases and their influence on the formation of polyunsaturated fatty acids, it should be noted that only small contents of delta-4-unsaturated fatty acids/lipids have been achieved through expression of the corresponding desaturase as described to date (see above). In addition, no specificity for the sn-2 position, which is important in terms of nutritional physiology, in glycerolipids is described for the abovementioned enzymes (Hunter, J E, Lipids 36(7):655-668, 2001).

Thus there remains a great need for novel and better suited genes which code for enzymes which are involved in the biosynthesis of unsaturated fatty acids and make it possible to produce certain fatty acids specifically on an industrial scale without unwanted byproducts being formed. Two features in particular are especially important in the selection of biosynthesis genes. Firstly, there is still a need for improved processes for obtaining maximal contents of polyunsaturated fatty acids. Secondly, the enzymes employed should be highly specific for a particular substrate, because ideally no unwanted byproducts possibly having adverse or as yet unresearched physiological effects in nutritional use may arise.

In order to make it possible to enrich human food and animal feed with the specifically prepared polyunsaturated fatty acids, there is thus a great need for a simple, costeffective process for producing these polyunsaturated fatty acids with the aid of enzymes which are as specific as possible and are involved in fatty acid biosynthesis.

BRIEF DESCRIPTION OF THE DRAWINGS

FIG. 1 shows the various synthetic pathways for the biosynthesis of DHA (docosahexaenoic acid).

FIG. 2 shows the sequence comparison of the Δ4-desaturases from *Euglena gracilis* and Thraustochytrium (WO 200226946). The two sequences show 35% identity [CLUSTAL W(1.60) multiple sequence alignment].

FIG. 3 shows the sequence comparison (GAP alignment) of the Δ4-desaturases from *Euglena gracilis* and Thraustochytrium (WO 200226946).

FIG. 4 shows the GC analyses of yeast cells fed with DPA (docosapentaenoic acid). Control: yeast cells without Δ4-desaturase [A], conversion to DHA in cells having the Δ4-desaturase (pYES-EGD4-2) [B].

FIG. 5 shows the position analysis of Δ4-desaturated fatty acids. 16:1 Δ7 and 22:4 Δ7,10,13,16 were used for feeding. Conversion is stated in percent.

The object therefore was to isolate novel nucleic acids which are involved as specifically as possible in the synthesis of these polyunsaturated fatty acids for the production of polyunsaturated fatty acids in an organism, advantageously in a eukaryotic organism, preferably in a plant. This object has been achieved by the inventive isolated nucleic acid sequences which code for polypeptides having Δ-4-desaturase activity selected from the group:

a) of a nucleic acid sequence having the sequence depicted in SEQ ID NO: 1,
b) nucleic acid sequences which, as a result of the degeneracy of the genetic code, can be derived from the coding sequence comprised in SEQ ID NO: 1, or
c) derivates of the nucleic acid sequence depicted in SEQ ID NO: 1, which code for polypeptides having the amino acid sequences depicted in SEQ ID NO: 2 and have at least 40% homology at the amino acid level with SEQ ID NO: 2 and have a Δ-4-desaturase activity.

It has surprisingly been found that a Δ4-desaturases from *Euglena gracilis* is particularly specific for conversion of docopentaenoic acid (DPA) into docohexaenoic acid (DHA) when they are expressed in a heterologous system. It is thus possible to produce docosahexaenoic acid in plants or microorganisms, in which case the specificity of the found enzyme greatly reduces the production of unwanted byproducts. Moreover, the double bond at the C4-C5 position of the fatty acid is introduced only when a double bond is already present in the C7-C8 position. The found enzyme can thus be used not only for the synthesis of DHA from DPA, but also for the synthesis of specific fatty acids which occur in nature to only a limited extent or not at all. Examples of such fatty acids are 16:2 Δ4, Δ7 or 16:3 Δ4, Δ7, Δ10, Δ13.

This distinguishes the found Δ4-desaturase, besides the enhanced specificity and activity, advantageously the prior art enzymes.

Since previously described Δ4-desaturase genes have only low activity and specificity, a further object of the invention was therefore to introduce specific desaturase enzyme for the synthesis of polyunsaturated long-chain fatty acids into the seeds of oil seeds and to avoid the production of unwanted byproducts. This object has been achieved by cloning the nucleic acid disclosed above.

The found Δ-4-desaturase differs from previously described Δ4-desaturases by substantially different nucleotide and amino acid sequences. The *Euglena* sequence shows only 35% similarity at the amino acid level to *Thraustochytrium* sequence (WO200226946). FIG. 2 shows a sequence comparison of the found *Euglena* sequence with the sequence from *Thraustochytrium*, and FIG. 3 shows the GAP alignment.

The term "Δ-4-desaturase" for the purposes of the invention comprises proteins which participate in the desaturation of fatty acids, advantageously of fatty acids which have a double bond in position 7 of the fatty acid chain, and their homologs, derivatives or analogs.

In a further embodiment, derivatives of the inventive nucleic acid molecule represented in SEQ ID NO: 1 encode proteins having at least 40%, advantageously about 50 to 60%, preferably at least about 60 to 70% and more preferably at least about 70 to 80%, 80 to 90%, 90 to 95% and most preferably at least about 96%, 97%, 98%, 99% or more homology (=identity) to the complete amino acid sequence of SEQ ID NO: 2. The homology was calculated over the entire amino acid or nucleic acid sequence region. The Pile Up program (J. Mol. Evolution., 25, 351-360, 1987, Higgins et al., CABIOS, 5 1989; 151-153) or the Gap and BestFit program [Needleman and Wunsch (J. Mol. Biol. 48; 443-453 (1970) and Smith and Waterman (Adv. Appl. Math. 2; 482-489 (1981)], which are comprised in the GCG software package [Genetics Computer Group, 575 Science Drive, Madison, Wis., USA 53711 (1991)], was used for the sequence comparisons. The sequence homologies indicated in percent above were found with the BestFit program over the entire sequence region, using the following settings: Gap Weight: 8, Length Weight: 2.

The invention additionally comprises nucleic acid molecules which differ from one of the nucleotide sequences shown in SEQ ID NO: 1 (and parts thereof) on the basis of the degeneracy of the genetic code, and thus encode the same Δ-4-desaturase as that encoded by the nucleotide sequence shown in SEQ ID NO: 1.

In addition to the Δ-4-desaturase nucleotide sequence shown in SEQ ID NO: 1, the skilled worker realizes that DNA sequence polymorphisms which lead to alterations in the amino acid sequences of the Δ-4-desaturase may exist within a population. These genetic polymorphisms in the Δ-4-desaturase gene may exist between individuals within a population owing to natural variation. These natural variants normally bring about a variation of from 1 to 5% in the nucleotide sequence of the Δ-4-desaturase gene. Each and all of these nucleotide variations and amino acid polymorphisms, resulting therefrom, in the Δ-4-desaturase, which are the result of the natural variation and do not alter the functional activity of the Δ-4-desaturase are to be comprised within the scope of the present invention.

Polyunsaturated fatty acids (PUFAS) mean hereinafter diunsaturated or polyunsaturated fatty acids having double bonds. The double bonds may be conjugated or unconjugated.

The inventive Δ-4-desaturase enzyme advantageously introduces a cis double bond in the $C_4$-$C_5$ position in fatty acid residues of glycerolipids (see SEQ ID NO: 1 and NO: 2). The enzyme additionally has a Δ-4-desaturase activity which advantageously introduces exclusively a cis double bond in the $C_4$-$C_5$ position in fatty acid residues of glycerolipids. The enzyme having the sequence specified in SEQ ID NO: 1 and NO: 2 also has this activity. The sequences depicted in SEQ ID NO: 1 and NO: 2 comprise a monofunctional Δ-4-desaturase.

The inventive nucleic acid sequence (or fragments thereof can advantageously be used to isolate further genomic sequences by homology screening.

Said derivatives can be isolated for example from other organisms eukaryotic organisms such as plants such as specifically mosses, dinoflagellates or fungi.

Allelic variants comprise in particular functional variants obtainable by deletion, insertion or substitution of nucleotides from the sequence depicted in SEQ ID NO: 1, with the enzymatic activity of the derived synthesized proteins being retained.

Such DNA sequences can be isolated starting from the DNA sequence described in SEQ ID NO: 1, or parts of these sequences, for example using conventional hybridization methods or the PCR technique, from other eukaryotes such as, for example, those mentioned above. These DNA sequences hybridize under standard conditions with the sequences mentioned. It is advantageous to use for the hybridization short oligonucleotides, for example of the conserved regions which can be found by comparisons with other desaturase genes in a manner known to the skilled worker. The histidine box sequences are advantageously used. However, it is also possible to use longer fragments of the inventive nucleic acids or the complete sequences for the hybridization. These standard conditions vary depending on the nucleic acid used: oligonucleotide, longer fragment or complete sequence or depending on which type of nucleic acid DNA or RNA are used for the hybridization. Thus, for example, the melting temperatures for DNA:DNA hybrids are about 10° C. lower than those of DNA:RNA hybrids of the same length.

Standard conditions mean for example depending on the nucleic acid temperatures between 42 and 58° C. in an aqueous buffer solution with a concentration of between 0.1 to 5×SSC (1×SSC=0.15 M NaCl, 15 mM sodium citrate, pH 7.2) or additionally in the presence of 50% formamide such as, for example, 42° C. in 5×SSC, 50% formamide. The hybridization conditions for DNA:DNA hybrids are advantageously at 0.1×SSC and temperatures between about 20° C. to 45° C., preferably between about 30° C. to 45° C. The hybridization conditions for DNA:RNA hybrids are advantageously at 0.1×SSC and temperatures between about 30° C. to 55° C., preferably between about 45° C. to 55° C. These stated temperatures for the hybridization are melting temperatures calculated by way of example for a nucleic acid having a length of about 100 nucleotides and a G+C content of 50% in the absence of formamide. The experimental conditions for the DNA hybridization are described in relavent text books of genetics such as, for example, Sambrook et al., "Molecular Cloning", Cold Spring Harbor Laboratory, 1989, and can be calculated by formulae known to the skilled worker, for example depending on the length of the nucleic acids, the nature of the hybrids or the G+C content. Further information on hybridization can be found in the following text books: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Derivatives additionally mean homologs of the sequence SEQ ID NO: 1, for example eukaryotic homologs, truncated sequences, single-stranded DNA of the coding and noncoding DNA sequence or RNA of the coding and noncoding DNA sequence.

Homologs of the sequence SEQ ID NO: 1 additionally mean derivatives such as, for example, promoter variants. These variants may be modified by one or more nucleotide exchangers, by insertion(s) and/or deletion(s), but without the functionality or activity of the promoters being impaired. It is additionally possible for the promoters to have their activity increased by modification of their sequence, or be completely replaced by more active promoters, even from heterologous organisms.

Derivates also advantageously mean variants whose nucleotide sequence in the region from −1 to −2000 in front of the start codon have been modified in such a way that gene expression and/or protein expression is altered, preferably increased. In addition, derivatives also mean variants which have been modified at the 3' end.

Derivatives also mean the antisense DNAs which can be used to inhibit protein biosynthesis of the inventive proteins. These antisense DNAs are among the inventive nonfunctional derivatives such as derivatives which have no enzymatic activity. Further methods, known to the skilled worker for preparing nonfunctional derivatives are the so-called cosuppression, the use of ribozymes and introns. Ribozymes are catalytic RNA molecules having ribonuclease activity which are able to cut single-stranded nucleic acids such as mRNA, to which they show a complementarity. It is thus possible for mRNA transcripts to be cleaved catalytically with the aid of these ribozymes (Haselhoff and Gerlach, Nature, 334, 1988: 585-591), and thus the translation of this mRNA to be suppressed. Such ribozymes can be tailored specifically for their tasks (U.S. Pat. No. 4,987,071; U.S. Pat. No. 5,116,742 and Bartel et al., Science 261, 1993: 141.1-1418). It is thus possible with the aid of antisense DNA to produce fatty acids, lipids or oils having an increased content of saturated fatty acids.

The inventive nucleic acid sequence which codes for a Δ-4-desaturase can be synthetically prepared or obtained naturally, or comprise a mixture of synthetic and natural DNA constituents, and consist of various heterologous Δ-4-desaturase gene segments from various organisms. In general, synthetic nucleotide sequences are produced using codons which are preferred by the corresponding host organisms, for example plants. This usually leads to optimal expression of the heterologous genes. These codons preferred by plants can be determined from codons with the highest protein frequency which are expressed in most plant species of interest. One example for *Corynebacterium glutamicum* is given in: Wada et al. (1992) *Nucleic Acids Res.* 20:2111-2118). The carrying out of such experiments can be carried out with the aid of standard methods and are known to the person skilled in the art.

Functionally equivalent sequences which code for the Δ-4-desaturase gene are those derivatives of the inventive sequence which, despite a differing nucleotide sequence, still have the desired functions, that is the enzymatic activity and specific selectivity of the proteins. Functional equivalents thus comprise naturally occurring variants of the sequences described herein, and artificial, e.g. obtained by chemical synthesis, artificial nucleotide sequences adapted to the codon usage of a plant.

Artificial DNA sequences are additionally suitable as long as they confer, as described above, the desired property, for example of increasing the content of Δ-4 double bonds in fatty acids, oils or lipids in the plant by overexpression of the Δ-4-desaturase gene in crop plants. Such artificial DNA sequence may, for example through back-translation by means of molecular modeling of constructed proteins, have Δ-4-desaturase activity or be found by in vitro selection. Possible techniques for the in vitro evolution of DNA to modify or improve the DNA sequences are described in Patten, P. A. et al., Current Opinion in Biotechnology 8, 724-733 (1997) or in Moore, J. C. et al., Journal of Molecular Biology 272, 336347 (1997). Coding DNA sequences obtained by back-translation of a polypeptide sequence in accordance with the codon usage specific for the host plant are particularly suitable. The specific-codon usage can easily be found by a skilled worker familiar with methods in plant genetics by computer analyses of other, known genes of the plant to be transformed.

Sequences which should be mentioned as further suitable equivalent nucleic acid sequences are those coding for fusion proteins, where a Δ-4-desaturase polypeptide or a functionally equivalent part thereof is a constituent of the fusion protein. The second part of the fusion protein may be for example a further polypeptide having enzymatic activity or an antigenic polypeptide sequence with the aid of which it is possible to detect Δ-4-desaturase expression (e.g. myc-tag or his-tag). However, it is preferably a regulatory protein sequence, for example a signal sequence for the ER, which guides the Δ-4-desaturase protein to the desired site of action.

The inventive isolated nucleic acid sequences are advantageously derived from a plant such as a monocotyledonous or dicotyledonous plant. The nucleic acid sequences are preferably derived from the class of Euglenophyceae such as the orders Eutreptiales, Euglenales, Rhabdomonadales, Sphenomonadales, Heteronematales or Euglenamorphales, particularly advantageously the sequences are derived from the genus and species *Euglena gracilis, Astasia longa, Khawkinea quartana, Phacus smulkowskianus, Lepocinclis ovum, Lepocinclis ovata, Eutreptia viridis, Distigma proteus, Distigma curvatum, Rhabdomonas intermedia, Rhabdomonas gibba, Rhabdomonas spiralis, Gyropaigne lefevrei, Rhabdomonas incurva, Peranema trichophorum* or *Petalomonas cantuscygni*, very particularly advantageously they are derived from *Euglena gracilis*.

It is possible and advantageous for the Δ-4-desaturase genes to be combined in the inventive process with further genes of fatty acid biosynthesis. Examples of such genes are acyltransferases, further desaturases or elongases. Combination with, for example, NADH-cytochrome B5 reductases able to take up or release reducing equivalents is advantageous for in vivo and specifically in vitro synthesis.

The inventive amino acid sequences mean proteins comprising an amino acid sequence depicted in the sequence SEQ ID NO: 2, or a sequence obtainable therefrom by substitution, inversion, insertion or deletion of one or more amino acid residues, with retention of or a negligible reduction in enzymatic activities of the protein depicted in SEQ ID NO: 2. Negligible reduction means all enzymes which still have at least 10%, preferably 20%, particularly preferably 30% of the enzymatic activity of the initial enzyme. It is possible in this connection for example for certain amino acids to be replaced by those having similar physicochemical properties (bulk, basicity, hydrophobicity etc.). For example, arginine residues are replaced by lysine residues, valine residues by isoleucine residues or aspartic acid residues by glutamic acid residues. However, it is also possible for one or more amino acids to be transposed in their sequence, added or deleted, or it is possible for a plurality of these measures to be combined together.

Derivates also mean functional equivalents which comprise in particular also natural or artificial mutations of an originally isolated sequence coding for Δ-4-desaturase, which still show the desired function, that is to say their enzymatic activity and substrate selectivity is negligibly reduced. Mutations comprise substitutions, additions, deletions, transpositions or insertions of one or more nucleotide residues. Thus, for example, the present invention also comprises those nucleotide sequences which are obtained by modification of the Δ-4-desaturase nucleotide sequence. The aim of such a modification may be for example further localization of the coding sequence comprised therein or, for example, also the insertion of further restriction enzyme cleavage sites.

Functional equivalents are also variants whose function, by comparison with the initial gene or gene fragment, is attenuated (=negligibly reduced) or enhanced (=enzymic activity greater than the activity of the initial enzyme, that is activity is higher than 100%, preferably higher than 110%, particularly preferably higher than 130%).

The nucleic acid sequence may moreover advantageously be for example a DNA or cDNA sequence. Coding sequences suitable for insertion into an inventive expression cassette are for example those which code for a Δ-4-desaturase having the sequences described above and which confer on the host the ability to overproduce fatty acids, oils or lipids having double bonds in the Δ-4 position, especially in the case where co 3 fatty acids having at least four double bonds are produced. These sequences may be of homologous or heterologous origin.

The inventive expression cassette (=nucleic acid construct or fragment) means the sequence specified in SEQ ID NO: 1 which as a result of the genetic code and/or its functional or nonfunctional derivatives which have been functionally linked to one or more regulatory signals advantageously to increase gene expression, and which control the expression of the coding sequence in the host cell. These regulatory sequences are intended to make targeted expression of the genes and of protein expression possible. This may mean for example depending on the host organism that the gene is expressed and/or overexpressed only after induction, or that it is immediately expressed and/or overexpressed. For example, these regulatory sequences are sequences to which the inducers or repressors bind and thus regulate the expression of the nucleic acid. In addition to these novel regulatory sequences or in place of these sequences it is possible for the natural regulation of these sequences still to be present in front of the actual structural genes and, where appropriate, to have been genetically modified so that the natural regulation has been switched off and expression of the genes has been increased. The gene construct may, however, also have a simpler structure, meaning that no additional regulatory signals have been inserted in front of the nucleic acid sequence or its derivatives, and the natural promoter with its regulation has not been deleted. Instead, the natural regulatory sequence has been mutated in such a way that regulation no longer takes place and/or gene expression is increased. These modified promoters can also be put in the form of partial sequences (=promoter with parts of the inventive nucleic acid sequences) also alone in front of the natural gene to increase the activity. The gene construct may additionally comprise advantageously also one or more so-called enhancer sequences functionally linked to the promoter, which make increased expression of the nucleic acid sequence possible. It is also possible to insert additional advantageous sequences at the 3' end of the DNA sequences, such as further regulatory elements or terminators. The Δ-4-desaturase gene may be present in one or more copies in the expression cassette (=gene construct).

The regulatory sequences or factors may moreover, as described above, advantageously have a positive influence on, and thus increase, gene expression of the inserted genes. Thus, an enhancement of the regulatory elements can advantageously take place at the transcription level by using strong transcription signals such as promoters and/or enhancers. However, it is also possible in addition to enhance translation by, for example, improving the stability of the mRNA.

Promoters suitable in the expression cassette are in principle all promoters able to control the expression of foreign genes in organisms, advantageously in plants or fungi. It is advantageous to use in particular a plant promoters or promoters derived from a plant virus. Advantageous regulatory sequences for the inventive process are present for example in promoters such as cos, tac, trp, tet, trp-tet, lpp, lac, lpp-lac, lacI$^{q-}$, T7, T5, T3, gal, trc, ara, SP6, λ-P$_R$ or in the λ-P$_L$ promoter, which are advantageously used in gram-negative bacteria. Further advantageous regulatory sequences are present for example in the gram-positive promoters amy and SPO2, in the yeast or fungal promoters ADC1, MFα, AC, P-60, CYC1, GAPDH, TEF, rp28, ADH or in the plant promoters such as CaMV/35S [Franck et al., Cell 21(1980) 285-294], SSU, OCS, lib4, STLS1, B33, nos (=nopaline synthase promoter) or in the ubiquitin promoter. The expression cassette may also comprise a chemically inducible promoter through which expression of the exogenous Δ-4-desaturase gene in the organisms, advantageously in the plants, can be controlled at a particular time. Examples of such advantageous plant promoters are the PRP1 promoter [Ward et al., Plant. Mol. Biol. 22(1993), 361-366], a benzenesulfonamide-inducible (EP 388186), a tetracycline-inducible (Gatz et al., (1992) Plant J. 2,397-404), a salicylic acid-inducible promoter (WO 95/19443), an abscisic acid-inducible (EP 335528) and an ethanol- or cyclohexanone-inducible (WO 93/21334) promoter. Further plant promoters are for example the promoter of the potato cytosolic FBPase, the potato ST-LSI promoter (Stockhaus et al., EMBO J. 8 (1989) 2445-245), the phosphoribosylpyrophosphate amidotransferase promoter from *Glycine max* (see also Genbank Accession Number U87999) or a node-specific promoter as in EP 249676 can advantageously be used. Advantageous plant promoters are in particular those which ensure expression in tissues or plant parts/organs in which fatty acid biosynthesis or precursors thereof takes place, such as, for example, in the endosperm or in the developing embryo. Particular mention should be made of advantageous promoters which ensure seed-specific expression, such as, for example, USP promoter or derivatives thereof, the LEB4 promoter, the phaseolin promoter or the napin promoter. The USP promoter, which is mentioned according to the invention and is particularly advantageous, or its derivatives mediate very early gene expression during seed development (Baeumlein et al., Mol Gen Genet, 1991, 225 (3): 459-67). Further advantageous seed-specific promoters which can be used for monocotyledonous and dicotyledonous plants are the promoters suitable for dicotyledons, such as, likewise mentioned by way of example, napin gene promoter from oilseed rape (U.S. Pat. No. 5,608,152), the oleosin promoter from *Arabidopsis* (WO 98/45461), the phaseolin promoter from *Phaseolus vulgaris* (U.S. Pat. No. 5,504,200), the *brassica* Bce4 promoter (WO 91/13980) or the legumin B4 promoter (LeB4, Baeumlein et al., Plant J., 2, 2, 1992: 233-239) or promoters suitable for monocotyledons such as the promoters the promoters of the barley lpt2 or lpt1 gene (WO 95/15389 and WO 95/23230), or the promoters of the barley hordein gene, of the rice glutelin gene, of the rice oryzin gene, of the rice prolamin gene, of the wheat gliadin gene, of the wheat glutelin gene, of the corn zein gene, of the oats glutelin gene, of the *sorghum* casirin gene or of the rye secalin gene, which are described in WO 99/16890.

In addition, particularly preferred promoters are those which ensure expression in tissues or plant parts in which, for example, biosynthesis of fatty acids, oils and lipids or their precursors takes place. Particular mention should be made of promoters which ensure seed-specific expression. Mention should be made of the promoter of the napin gene from oilseed rape (U.S. Pat. No. 5,608,152), of the USP promoter from *Vicia faba* (USP=unknown seed protein, Baeumlein et al., Mol Gen Genet, 1991, 225 (3): 459-67), of the oleosin gene from *Arabidopsis* (WO 98/45461), of the phaseolin promoter (U.S. Pat. No. 5,504,200) or of the promoter of the legumin B4 gene (LeB4; Baeumlein et al., 1992, Plant Journal, 2 (2): 233-9). Additional mention should be made of promoters like that of barley lpt2 or lpt1 gene (WO 95/15389 and WO 95/23230), which mediate seed-specific expression in monocotyledonous plants.

The expression cassette (=gene construct, nucleic acid construct) may, as described above, also comprise further genes which are to be introduced into the organisms. These genes may be under separate regulation or under the same regulatory region as the Δ-4-desaturase gene. These genes are for example further biosynthesis genes, advantageously of fatty acid biosynthesis such as biosynthesis genes of fatty acid or lipid metabolism, which make increased synthesis possible, selected from the group of acyl-CoA dehydrogenase(s), acyl-ACP [=acyl carrier protein] desaturase(s), acyl-ACP thioesterase(s), fatty acid acyltransferase(s), acyl-COA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s). Examples which may be mentioned are the genes for the Δ-15-, Δ-12-, Δ-9-, Δ-6-, Δ-5-desaturases, β-ketoacyl reductases, β-ketoacyl synthases, elongases or the various hydroxylases and acyl-ACP thioesterases. It is advantageous to use desaturase and elongase genes in the nucleic acid construct. It is particularly advantageous to use genes selected from the group of Δ-4-desaturase, Δ-5-desaturase, Δ-6-desaturase, Δ-8-desaturase, Δ-9-desaturase, Δ-12-desaturase, Δ-5-elongase, Δ-6-elongase or Δ-9-elongase in the construct.

It is also possible in principle to use all natural promoters with their regulatory sequences like those mentioned above for the inventive expression cassette and the inventive process as described below. It is additionally possible and advantageous to use synthetic promoters.

It is possible in the preparation of an expression cassette to manipulate various DNA fragments in order to obtain a nucleotide sequence which expediently reads in the correct direction and which is equipped with a correct reading frame. Adapters or linkers can be attached to the fragments for joining the DNA fragments (=inventive nucleic acids) to one another.

It is expediently possible for the promoter and terminator regions to be provided in the direction of transcription with a linker or polylinker which comprises one or more restriction sites for insertion of this sequence. The linker usually has from 1 to 10, mostly 1 to 8, preferably 2 to 6, restriction sites. The linker generally has a size within the regulatory regions of less than 100 bp, frequently less than 60 bp, but at least 5 bp. The promoter may be both natural or homologous and heterologous to the host organism, for example to the host plant. The expression cassette comprises in the 5'-3' transcription direction the promoter, a DNA sequence which codes for a Δ-4-desaturase gene, and a region for termination of transcription. Various termination regions are mutually exchangeable as desired.

A further possibility is to employ manipulations which provide appropriate restriction cleavage sites or which delete superfluous DNA or restriction cleavage sites. Where insertions, deletions or substitutions such as, for example, transitions and transversions come into consideration, it is possible to use in vitro mutagenesis, primer repair, restriction or ligation. In the case of suitable manipulations such as, for example, restriction, chewing back or filling in of overhangs for blunt ends, it is possible to provide complementary ends of the fragments for the ligation.

It may be important for advantageous high expression inter alia to attach the specific ER retention signal SEKDEL (Schouten, A. et al., Plant Mol. Biol. 30 (1996), 781-792) in that the average level of expression is thereby tripled or quadrupled. It is also possible to employ other retention signals which occur naturally in associaton with plant and animal proteins localized in the ER for the construction of the cassette.

Preferred polyadenylation signals are plant polyadenylation signals, preferably those essentially corresponding to T-DNA polyadenylation signals from Agrobacterium tumefaciens, especially of gene 3 of T-DNA (octopine synthase) of the Ti plasmid pTiACH5 (Gielen et al., EMBO J.3 (1984), 835 ff) or appropriate functional equivalents.

An expression cassette is prepared by fusing a suitable promoter to a suitable Δ-4-desaturase DNA sequence and to a polyadenylation signal by conventional techniques of recombination and cloning as described for example in T. Maniatis, E. F. Fritsch and J. Sambrook, Molecular Cloning: A Laboratory Manual, Cold Spring Harbor Laboratory, Cold Spring Harbor, N.Y. (1989), and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

It is possible in the preparation of an expression cassette to manipulate various DNA fragments in order to obtain a nucleotide sequence which expediently reads in the correct direction and which is equipped with a correct reading frame. Adapters or linkers can be attached to the fragments for joining the DNA fragments to one another.

It is expediently possible for the promoter and terminator regions to be provided in the direction of transcription with a linker or polylinker which comprises one or more restriction sites for insertion of this sequence. The linker usually has from 1 to 10, mostly 1 to 8, preferably 2 to 6, restriction sites. The linker generally has a size within the regulatory regions of less than 100 bp, frequently less than 60 bp, but at least 5 bp. The promoter may be both natural or homologous and heterologous to the host organism, for example to the host plant. The expression cassette comprises in the 5'-3' transcription direction the promoter, a DNA sequence which codes for a Δ-4desaturase gene, and a region for termination of transcription. Various termination regions are mutually exchangeable as desired.

It is possible in the preparation of an expression cassette to manipulate various DNA fragments in order to obtain a nucleotide sequence which expediently reads in the correct direction and which is equipped with a correct reading frame. Adapters or linkers can be attached to the fragments for joining the DNA fragments to one another.

It is expediently possible for the promoter and terminator regions to be provided in the direction of transcription with a linker or polylinker which comprises one or more restriction sites for insertion of this sequence. The linker usually has from 1 to 10, mostly 1 to 8, preferably 2 to 6, restriction sites. The linker generally has a size within the regulatory regions of less than 100 bp, frequently less than 60 bp, but at least 5 bp. The promoter may be both natural or homologous and heterologous to the host organism, for example to the host plant. The expression cassette comprises in the 5'-3' transcription direction the promoter, a DNA sequence which codes for a Δ-4-desaturase gene, and a region for termination of transcription. Various termination regions are mutually exchangeable as desired.

The DNA sequences coding for two Δ-4-desaturases from Euglena gracilis comprises all the sequence features necessary to achieve localization correct for the site of fatty acid, lipid or oil biosynthesis. For this reason, no further targeting sequences are necessary per se. However, such a localization may be desirable and advantageous and therefore be artificially modified or enhanced so that such fusion constructs are also a preferred advantageous embodiment of the invention.

Particularly preferred sequences are those which ensure targeting in plastids. Targeting in other compartments may also in certain circumstances be desirable (reference: Kermode, Crit. Rev. Plant Sci. 15, 4 (1996), 285-423) e.g. into the vacuole, into the mitochondrion, into the endoplasmic reticulum (ER), peroxisomes, lipid bodies or else owing to absence of corresponding operative sequences remaining in the compartment of production, the cytosol.

It is advantageous for the inventive nucleic acid sequences to be cloned together with at least one reporter gene into an expression cassette which is introduced into the organism via a vector or directly into the genome. This reporter gene should make detectability easy via a growth, fluorescence, chemo-, bioluminescence or resistance assay or via a photometric measurement. Examples which may be mentioned of reporter genes are antibiotic- or herbicide-resistent genes, hydrolase genes, fluorescent protein genes, bioluminescence genes, sugar or nucleotide metabolism genes or biosynthesis genes such as the Ura3 gene, the Ilv2 gene, the luciferase gene, the α-galactosidase gene, the gfp gene, the 2-deoxyglucose-6-phosphate phosphatase gene, the β-glucuronidase gene, β-lactamase gene, the neomycin phosphotransferase gene, the hygromycin phosphotransferase gene or the BASTA (=gluphosinate resistance) gene. These genes make easy measurability and quantifyability of the transcription activity, and thus of the expression of the genes, possible. It is thus possible to identify genome sites showing differences in productivity.

In a preferred embodiment, an expression cassette comprises upstream, i.e. at the 5' end of the coding sequence, a promoter and downstream, i.e. at the 3' end, a polyadenylation signal and, where appropriate, further regulatory elements which are operatively linked to the coding sequence for the Δ-4-desaturase and/or Δ-4-desaturase DNA sequence lying inbetween. Operative linkage means sequential arrangement of promoter, coding sequence, terminator and, where appropriate, further regulatory elements in such a way that each of the regulatory elements can carry out its function in the expression of the coding sequence as intended. The sequences preferred for operative linkage are targeting sequences for ensuring subcellular localization in plastids. However, targeting sequences for ensuring subcellular localization in the mitochondrion, in the endoplasmic reticulum (ER), in the cell nucleus, in elaioplasts or other compartments can be employed if required, as can translation enhancers such as the 5'-leader sequence from the tobacco mosaic virus (Gallie et al., Nucl. Acids Res. 15 (1987), 8693-8711).

An expression cassette may comprise for example a constitutive promoter (preferably the USP or napin promoter), the gene to be expressed and the ER retention signal. The ER retention signal preferably used is the amino sequence KDEL (lysine, aspartic acid, glutamic acid, leucine).

For expression in a prokaryotic or eukaryotic host organism, for example a microorganism such as a fungus or a plant, the expression cassette is advantageously inserted into a vector such as, for example, a plasmid, a phage or other DNA which makes optimal expression of the genes in the host organism possible. Suitable plasmids are for example in *E. coli* pLG338, pACYC184, pBR series such as, for example, pBR322, pUC series such as pUC18 or pUC1 g, M113 mp series, pKC30, pRep4, pHS1, pHS2, pPLc236, pMBL24, pLG200, pUR290, pIN-III$^{113}$-B1, λgt11 or pBdCl, in *streptomyces* pIJ101, pIJ364, pIJ702 or pIJ361, in *bacillus* pUB110, pC194 or pBD214, in *corynebacterium* pSA77 or pAJ667, in fungi pALS1, pIL2 or pBB116; further advantageous fungal vectors are described by Romanos, M. A. et al., [(1992) "Foreign gene expression in yeast: a review", *Yeast* 8: 423-488] and by van den Hondel, C. A. M. J. J. et al. [(1991) "Heterologous gene expression in filamentous fungi] and in More Gene Manipulations in Fungi [J. W. Bennet & L. L. Lasure, eds., p. 396-428: Academic Press: San Diego] and in "Gene transfer systems and vector development for filamentous fungi [van den Hondel, C. A. M. J. J. & Punt, P. J. (1991) in: Applied Molecular Genetics of Fungi, Peberdy, J. F. et al., eds., p. 1-28, Cambridge University Press: Cambridge]. Advantageous yeast promoters are, for example, 2∝M, pAG-1, YEp6, YEp13 or pEMBLYe23. Examples of algal or plant promoters are pLGV23, pGHlac+, pBIN19, pAK2004, pVKH or pDH51 (see Schmidt, R. and Willmitzer, L., 1988). The abovementioned vectors or derivatives of the aforementioned vectors represent a small selection of the possible plasmids. Further plasmids are well known to the skilled worker and can be found for example in the book Cloning Vectors (Eds. Pouwels P. H. et al. Elsevier, Amsterdam-New York-Oxford, 1985, ISBN 0 444 904018). Suitable plant vectors are described inter alia in "Methods in Plant Molecular Biology and Biotechnology" (CRC Press), Chapters 6/7, pages 71-119. Advantageous vectors are so-called shuttle vectors or binary vectors which replicate in *E. coli* and *agrobacterium*.

Vectors mean apart from plasmids also all other vectors known to the skilled worker, such as, for example phages, viruses such as SV40, CMV, baculovirus, adenovirus, transposons, IS elements, phasmids, phagemids, cosmids, linear or circular DNA. These vectors may undergo autonomous replication in the host organism or chromosomal replication; chromosomal replication is preferred.

In a further embodiment of the vector, the inventive expression cassette can also be introduced advantageously in the form of a linear DNA into the organisms, and be integrated by heterologous or homologous recombination into the genome of the host organism. This linear DNA may be composed of a linearized plasmid or only of the expression cassette as vector or the inventive nucleic acid sequences.

In a further advantageous embodiment, the inventive nucleic acid sequence can also be introduced alone into an organism.

If further genes besides the inventive nucleic acid sequence are to be introduced into the organism, they can be introduced all together with a reporter gene in a single vector or each individual gene with a reporter gene in a vector in each case into the organism, it being possible to introduce the different vectors at the same time or successively.

The vector advantageously comprises at least one copy of the inventive nucleic acid sequences and/or of the inventive expression cassette.

It is possible by way of example to incorporate the plant expression cassette in the transformation vector pRT ((a) Toepfer et al., 1993, Methods Enzymol., 217: 66-78; (b) Toepfer et al. 1987, Nucl. Acids. Res. 15: 5890 ff.).

Alternatively, a recombinant vector (=expression vector) can also be transcribed and translated in vitro, e.g. through use of the T7 promoter and of T7 RNA polymerase.

Expression vectors used in prokaryotes frequently utilize inducible systems with and without fusion proteins or fusion obligopeptides, it being possible for these fusions to take place both Kn-terminally and C-terminally or other useable domains of a protein. Such fusion vectors are ordinarily used for: i.) increasing the RNA expression rate ii.) increasing the achieveable protein synthesis rate, iii.) increasing the solubility of the protein, iv.) or simplifying purification through a binding sequence which can be used for affinity chromatography. Proteolytic cleavage sites are often also introduced via fusion proteins, enabling elimination of part of the fusion protein also of purification. Such recognition sequences for proteases recognized are for example factor Xa, thrombin and enterokinase.

Typical advantageous fusion and expression vectors are pGEX [Pharmacia Biotech Inc; Smith, D. B. and Johnson, K. S. (1988) *Gene* 67: 3140], pMAL (New England Biolabs, Beverly, Mass.) and pRIT5 (Pharmacia, Piscataway, N.J.), which comprises glutathione S-transferase (GST), maltose binding protein, or protein A.

Further examples of *E. coli* expression vectors are pTrc [Amann et al., (1988) *Gene* 69:301-315] and pET vectors [Studier et al., Gene Expression Technology: Methods in Enzymology 185, Academic Press, San Diego, Calif. (1990) 60-89; Stratagene, Amsterdam, The Netherlands].

Further advantageous vectors for use in yeast are pYepSec1 (Baldari, et al., (1987) *Embo J* 6:229-234), pMFa (Kurjan and Herskowitz, (1982) *Cell* 30:933-943), pJRY88 (Schultz et al., (1987) *Gene* 54:113-123), and pYES-Derivate (Invitrogen Corporation, San Diego, Calif.). Vectors for use in filamentous fungi are described in: van den Hondel, C. A. M. J. J. & Punt, P. J. (1991) "Gene transfer systems and vector development for filamentous fungi, in: Applied Molecular Genetics of Fungi, J. F. Peberdy, et al., eds., pp. 1-28, Cambridge University Press: Cambridge.

An alternative possibility is also to use advantageously insect cell expression vectors, e.g. for expression in Sf 9 cells. Examples thereof are the vectors of the pAc series (Smith et al. (1983) *Mol. Cell Biol.* 3:2156-2165) and of the pVL series (Lucklow and Summers (1989) *Virology* 170:31-39).

Plant cells or algae cells can additionally be used advantageously for gene expression. Examples of plant expression vectors are to be found in Becker, D., et al. (1992) "New plant binary vectors with selectable markers located proximal to the left border", *Plant Mol. Biol.* 20: 1195-1197 or in Bevan, M. W. (1984) "Binary *Agrobacterium* vectors for plant transformation", Nuc. Acid. Res. 12: 8711-8721.

The inventive nucleic acid sequences may additionally be expressed in mammalian cells. Examples of corresponding expression vectors are pCDM8 and pMT2PC mentioned in: Seed, B. (1987) *Nature* 329:840 or Kaufman et al. (1987) *EMBO J.* 6: 187-195). Promoters preferably to be used in this case are of viral origin such as, for example, promoters of the polyoma, adenovirus 2, cytomegalovirus or simian virus 40. Further prokaryotic and eukaryotic expression systems are mentioned in Chapters 16 and 17 in Sambrook et al., *Molecular Cloning: A Laboratory Manual. 2nd, ed., Cold Spring Harbor Laboratory*, Cold Spring Harbor Laboratory Press, Cold Spring Harbor, N.Y., 1989.

The introduction of the inventive nucleic acids, of the expression cassette or of the vector into organisms, for example into plants, can in principle take place by all methods known to the skilled worker.

Methods appropriate for microorganisms can be found by the skilled worker in the text books by Sambrook, J. et al. (1989) Molecular cloning: A laboratory manual, Cold Spring Harbor Laboratory Press, by F. M. Ausubel et al. (1994)

Current protocols in molecular biology, John Wiley and Sons, by D. M. Glover et al., DNA Cloning Vol. 1, (1995), IRL Press (ISBN 019-963476-9), by Kaiser et al. (1994) Methods in Yeast Genetics, Cold Spring Habor Laboratory Press or Guthrie et al. Guide to Yeast Genetics and Molecular Biology, Methods in Enzymology, 1994, Academic Press.

The transfer of foreign genes into the genome of a plant is referred to as transformation. In this case, the methods described for transformation and regeneration of plants from plant tissues or plant cells are utilized for transient or stable transformation. Suitable methods are protoplast transformation by polyethylene glycol-induced DNA uptake, the biolistic method with the gene gun—the so-called particle bombardment method, electroporation, incubation of dry embryos in DNA-containing solution, microinjection and agrobacterium-mediated gene transfer. Said processes are described, for example, in B. Jenes et al., Techniques for Gene Transfer, in: Transgenic Plants, Vol. 1, Engineering and Utilization, edited by S. D. Kung and R. Wu, Academic Press (1993) 128-143 and in Potrykus Annu. Rev. Plant Physiol. Plant Molec. Biol. 42 (1991) 205-225). The construct to be expressed is preferably cloned into a vector which is suitable for transforming *Agrobacterium tumefaciens*, for example pBin19 (Bevan et al., Nucl. Acids Res. 12 (1984) 8711). *Agrobacteria* transformed with such a vector can then be used in a known manner for transforming plants, especially crop plants such as, for example, tobacco plants by, for example, bathing wounded leaves or pieces of leaves in a solution of *agrobacteria* and then cultivating in suitable media. Transformation of plants with *Agrobacterium tumefaciens* is described for example by Höfgen and Willmitzer in Nucl. Acid Res. (1988) 16, 9877, or is disclosed inter alia in F. F. White, Vectors for Gene Transfer in Higher Plants; in Transgenic Plants, Vol. 1, Engineering and Utilization, herausgegeben von S. D. Kung und R. Wu, Academic Press, 1993, pages 15-38.

*Agrobacteria* transformed with an inventive expression vector can likewise be used in a known manner for transforming plants such as test plants such as *arabidopsis* or crop plants such as cereals, corn, oats, rye, barley, wheat, soybean, rice, cotton, sugarbeet, canola, sunflower, flax, hemp, potato, tobacco, tomato, carrot, paprika, oilseed rape, tapioca, manioc, arrowroot, tagetes, alfalfa, lettuce and the various tree, nut and vine species, in particular oil-bearing crop plants such as soybean, peanut, *ricinus*, sunflower, corn, cotton, flax, oilseed rape, coconut, oil palm, safflower (*Carthamus tinctorius*) or cocoa bean, e.g. by bathing wounded leaves or pieces of leaves in a solution of *agrobacteria* and then cultivating in suitable media. Particularly suitable for producing PUFAs, for example stearidonic acid, eicosapentaenoic acid and docosahexaenoic acid, are borage or primulaceae. Flax is particularly advantageously suitable for producing PUFAS having the inventive nucleic acid sequences advantageously in combination with further desaturases and elongases.

The genetically modified plant cells can be regenerated by all methods known to the skilled worker. Appropriate methods can be found in the abovementioned publications by S. D. Kung and R. Wu, Potrykus or Höfgen and Willmitzer.

Transgenic or host organisms suitable and advantageous in principle for the inventive nucleic acid, the expression cassette or the vector are all organisms able to synthesize fatty acids, specifically unsaturated fatty acids, and suitable for the expression of recombinant genes, such as microorganisms, nonhuman animals or plants. Examples which may be mentioned are plants such as *arabidopsis*, asteraceae such as *calendula* or crop plants such as soybean, peanut, *ricinus*, sunflower, corn, cotton, flax, oilseed rape, coconut, oil palm, safflower (*Carthamus tinctorius*) or cocoa bean, microorganisms such as fungi for example the genus *Mortierella*, *Saprolegnia* or *Pythium*, bacteria such as the genus *Escherichia*, yeasts such as the genus *Saccharomyces*, cyanobacteria, ciliates, algae or protozoa such as dinoflagellates such as Crypthecodinium. Preference is given to organisms able naturally to synthesize oils in relatively large amounts, such as fungi such as *Mortierella alpina, Pythium insidiosum* or plants such as soybean, oilseed rape, coconut, oil palm, safflower, *ricinus, calendula*, peanut, cocoa bean or sunflower or yeasts such as *Saccharomyces cerevisiae*, and particular preference is given to soya bean, oilseed rape, sunflower, flax, *calendula* or *Saccharomyces cerevisiae*. Transgenic animals are in principle also suitable as host organisms, for example *C. elegans*.

By transgenic organism or transgenic plant for the purposes of the invention is meant that the nucleic acids used in the process are not at their natural site in the genome of an organism, and the nucleic acids may be expressed homologously or heterologously. Transgenic also means, however, as mentioned, that the inventive nucleic acids are in their natural place in the genome of an organism, but that the sequence has been modified by comparison with the natural sequence and/or the regulatory sequences have been modified of the natural sequences. Transgenic is preferably expression of the inventive nucleic acids at a non-natural site in the genome, meaning that homologous or preferably heterologous expression of the nucleic acids occurs. Preferred transgenic organisms are fungi such as *Mortierella* or plants are the oil seed plants.

"Transgenic" thus means for example in relation to a nucleic acid sequence, an expression cassette or a vector comprising a nucleic acid sequence which codes for the Δ-4-desaturase or derivatives thereof, or an organism transformed with this nucleic acid sequence, an expression cassette or a vector, all constructions which have been assembled by genetic engineering methods and in which either a) the Δ-4-desaturase nucleic acid sequence, or b) a genetic control sequence functionally linked to the Δ-4-desaturase nucleic acid sequence, for example a promoter, or c) (a) and (b)

are not in their natural genetic environment or have been modified by genetic engineering methods, where the modification may be for example substitutions, additions, deletions, inversion or insertions of one or more nucleotide residues. Natural genetic environment means the natural chromosomal locus in the original organism or the presence in a genomic library. In the case of a genomic library, the natural genetic environment of the nucleic acid sequence is preferably at least partly retained. The environment flanks the nucleic acid sequence on at least one side and has a sequence length of at least 50 bp, preferably at least 500 bp, particularly preferably at least 1000 bp, very particularly preferably at least 5000 bp.

Host cells which can be used are moreover mentioned in: Goeddel, *Gene Expression Technology: Methods in Enzymology* 185, Academic Press, San Diego, Calif. (1990).

Expression strains which can be used, e.g. those having lower protease activity, are described in: Gottesman, S., *Gene Expression Technology: Methods in Enzymology* 185, Academic Press, San Diego, Calif. (1990) 119-128.

A further aspect of the invention relates to the use of an expression cassette comprising DNA sequences coding for a Δ-4-desaturase gene or DNA sequences hybridizing therewith for the transformation of plant cells and tissues or parts of plants. The aim of the use is to increase the content of fatty acids, oils or lipids having increased content of and double bonds in the Δ-4 position.

It is possible in this connection, depending on the choice of the promoter, for the expression of the Δ-4-desaturase gene to take place specifically in the leaves, in the seeds, the tubers or other parts of the plant. Such transgenic plants overproducing fatty acids, oils or lipids having Δ-4 double bonds, their propagation material, and their plant cell, tissues or parts are a further aspect of the invention. A preferred aspect according to the invention are transgenic plant comprising an inventive functional or nonfunctional (=antisense DNA or enzymatic inactive enzyme) nucleic acid sequence or a functional or nonfunctional expression cassette.

The expression cassette or the inventive nucleic acid sequences comprising a Δ-4-desaturase gene sequence may moreover also be employed for the transformation of the organisms mentioned by way of example above, such as bacteria, cyanobacteria, yeasts, filamentous fungi, ciliates and algae with the aim of increasing the content of fatty acids, oils or lipids Δ-4 double bonds.

Increasing the content of fatty acids, oils or lipids having Δ-4 double bonds means for the purposes of the present invention for example the artificially acquired capability of increased biosynthetic efficiency through functional overexpression of the Δ-4-desaturase gene in the inventive organisms, advantageously in the inventive transgenic plants compared with initial plants which have not been modified by genetic engineering at least for the duration of at least one plant generation.

The site of biosynthesis of fatty acids, oils or lipids for example is generally the seed or cell layers of the seed, so that seed-specific expression of the Δ-4-desaturase gene is worthwhile. However, it is obvious that the biosynthesis of fatty acids, oils or lipids need not be confined to the seed tissue but may also take place tissue-specifically in all other parts of the plant—for example in epidermis cells or in the tubers.

In addition, constitutive expression of the exogeneous Δ-4-desaturase gene is advantageous. However, on the other hand, inducible expression may also appear to be desirable.

The effectiveness of expression of the Δ-4-desaturase gene can be determined for example in vitro by shoot meristem propagation. In addition, a change in the nature and level of expression of the Δ-4-desaturase gene and the effect thereof on the efficiency of fatty acid, oil or lipid biosynthesis can be tested on test plants in greenhouse experiments.

The invention additionally relates to transgenic plants transformed with an expression cassette comprising a Δ-4-desaturase gene sequence or DNA sequences hybridizing therewith, and to transgenic cells, tissues, parts and propagation material of such plants. Particular preference is given in this connection to transgenic crop plants such as, for example, barley, wheat, rye, oats, corn, soybean, rice, cotton, sugarbeet, oilseed rape and canola, sunflower, flax, hemp, potato, tobacco, tomato, oilseed rape, tapioca, manioc, arrowroot, alfalfa, lettuce and the various tree, nut and vine species.

Plants for the purposes of the invention are mono- and dicotyledonous plants, mosses or algae.

A further inventive development are, as described above, transgenic plants comprising a functional or nonfunctional inventive nucleic acid sequence or a functional or nonfunctional inventive expression cassette. Nonfunctional means that enzymatically active protein is no longer synthesized. In addition, nonfunctional nucleic acids or nucleic acid constructs also mean a so-called antisense DNA which leads to transgenic plants which have a reduction in the enzymatic activity or no enzymatic activity. It is possible with the aid of the antisense technique, specifically if the inventive nucleic acid sequence is combined with other fatty acid synthesis genes in the antisense DNA, to synthesize triglycerides having an increased content of saturated fatty acids or to synthesize fatty acids. Transgenic plants mean single plant cells and cultures thereof on solid media or in liquid culture, parts of plants and whole plants.

Further aspects of the invention are:
Process for the transformation of a plant which comprises introducing inventive expression cassettes comprising a Δ-4-desaturase gene sequence from primulaceae or DNA' sequences hybridizing therewith into a plant cell, into callus tissue, a whole plant or protoplasts of plants.
Use of a Δ-4-desaturase DNA gene sequence or DNA sequences hybridizing therewith for producing plants having an increased content of fatty acids, oils or lipids having Δ-4 double bonds through expression of this Δ-4-desaturase DNA sequence in plants.
Proteins comprising the amino acid sequences depicted in SEQ ID NO: 2.
Use of the proteins having the sequences SEQ ID NO: 2 for producing unsaturated fatty acids.

A further aspect according to the invention is a process for producing unsaturated fatty acids, which comprises putting at least one inventive nucleic acid sequence described above or at least one inventive nucleic acid construct into a preferably oil-producing organism, culturing this organism and isolating that oil present in the organism, and liberating the fatty acids contained in the oil. These unsaturated fatty acids advantageously comprise Δ-4 double bonds. The fatty acids can be liberated from the oils or lipids for example by basic hydrolysis e.g. with NaOH or KOH.

The aspects of the invention also include a process for producing triglycerides having an increased content of unsaturated fatty acids, which comprises putting at least one inventive nucleic acid sequence described above or at least one inventive expression cassette into an oil-producing organism, culturing this organism and isolating that oil present in the organism.

A further aspect according to the invention is a process for producing triglycerides having an increased content of unsaturated fatty acids by incubating triglycerides having saturated or unsaturated or saturated and unsaturated fatty acids with at least the protein encoded by the sequence SEQ ID NO: 1. The process is advantageously carried out in the presence of compounds able to take up or release reducing equivalents. The fatty acids can then be liberated from the triglycerides.

Transgenic plants are advantageously used as organisms in the inventive process. These plants comprise the polyunsaturated fatty acids synthesized in the inventive process and can advantageously be marketed directly without the need to isolate the synthetic oils, lipids or fatty acids. Under plants in the inventive process are whole plants and all parts of plants, plant organs or parts of plants such as leaf, stalk, seed, root, tubers, anthers, fibers, root hairs, stems, embryos, calli, cotelydons, petiols, harvest material, plant tissue, reproductive tissue, cell cultures which are derived from the transgenic plants and/or can be used to produce the transgenic plant. The seed comprises in this connection all parts of seeds such as the seed coats, epidermal and seed cells, endosperm or embryonic tissue. The compounds produced in the inventive process may, however, also be isolated from the organisms, advantageously plants, in the form of their oils, fat, lipids and/or free fatty acids. Polyunsaturated fatty acids produced by this process can be harvested by harvesting the organisms either from the culture in which they are growing, or from the field. This can take place by pressing or extraction of the parts of the plants, preferably of the plant seeds. It is moreover possible for the oils, fats, lipids and/or free fatty acids to be obtained by pressing so-called cold beating or cold pressing without input of heat. So that the parts of plants, specifically the seeds, can be more easily disrupted, they are previously comminuted, steamed or roasted. The seeds pretreated in this way can then be pressed or be extracted with solvent such as hot hexane. The solvent is then removed again. In the case of microorganisms, after harvesting they are for example extracted directly without further operations or else extracted after disruption by various methods known to the skilled worker. It is possible in this way to isolate more than 96% of the compounds produced in the process. Subsequently, the products obtained in this way are further processed, i.e. refined. This entails initially for example the plant mucilages and suspended matter being removed. So-called desliming can take place enzymatically or for example chemically/physically by addition of acid such as phosphoric acid. The free fatty acids are then removed by treatment with a base, for example sodium hydroxide solution. The resulting product is thoroughly washed with water to remove the alkali remaining in the product and is dried. The products are subjected to a bleaching with, for example, Fuller's earth or activated carbon in order to remove pigments still present in the product. Finally, the product is also deodorized also for example with steam.

The PUFAs produced in the process advantageously result in the organisms in the form of their oils, lipids or fatty acids or fractions thereof.

A further inventive embodiment is the use of the oil, lipid, of the fatty acids and/or of fatty acid composition in animal feeds, human foods, cosmetics or pharmaceuticals.

The term "oil", "lipid" or "fat" means a fatty acid mixture which comprises unsaturated, saturated, preferably esterified fatty acid(s). It is preferred for the oil, lipid or fat to have a high content of polyunsaturated free or advantageously esterified fatty acid(s), in particular linoleic acid, γ-linolenic acid, dihomo-γ-linolenic acid, arachidonic acid, α-linolenic acid, stearidonic acid, eicosatetraenoic acid, eicosapentaenoic acid, docosapentaenoic acid or docosahexaenoic acid. The content of unsaturated esterified fatty acids is preferably about 30%, more preferably the content is 50%, even more preferably the content is 60%, 70%, 80% or more. For determination, for example the content of fatty acid can be determined by gas chromatography after the fatty acids have been converted into the methyl esters by transesterification. The oil, lipid or fat may comprise various other saturated or unsaturated fatty acids, e.g. calendulic acid, palmitic, palmitoleic, stearic, oleic acid etc. It is possible in particular for the content of the various fatty acids in the oil or fat to vary depending on the initial organism.

The polyunsaturated fatty acids produced in the process are, for example, sphingolipids, phosphoglycerides, lipids, glycolipids, phospholipids, monoacylglycerol, diacylglycerol, triacylglycerol or other fatty acid esters.

The polyunsaturated fatty acids present can be liberated from the polyunsaturated fatty acids which have been produced in this way in the inventive process and advantageously have at least two double bonds as described above for example by an alkali treatment, for example aqueous KOH or NaOH or acid hydrolysis advantageously in the presence of an alcohol such as methanol or ethanol or by an enzymatic elimination, and be isolated by, for example, phase separation and subsequent acidification with, for example, $H_2SO_4$. The liberation of the fatty acids can also take place directly without the working up described above.

The abovementioned processes advantageously make it possible to synthesize fatty acids or triglycerides having an increased content of fatty acids having Δ-4 double bonds.

The abovementioned processes advantageously make it possible to synthesize fatty acids or triglycerides having an increased content of fatty acids having Δ-4 double bonds, using substrate for the reaction of the Δ4-desaturase preferably docosapentaenoic acid. The abovementioned process thus advantageously makes it possible in particular to synthesize fatty acids such as, for example, docosahexaenoic acid.

It is also possible with the aid of so-called antisense technology to produce fatty acids or triglycerides having an increased content of saturated fatty acids in a process.

Examples of organisms which may be mentioned for said processes are plants such as *arabidopsis*, primulaceae, borage, barley, wheat, rye, oats, corn, soybean, rice, cotton sugarbeet, oilseed rape and canola, sunflower, flax, hemp, potato, tobacco, tomato, oilseed rape, tapioca, manioc, arrowroot, alfalfa, peanut, *ricinus*, coconut, oil palm, safflower (*Carthamus tinctorius*) or cocoa bean, microorganisms such as fungi *Mortierella, Saprolegnia* or *Pythium*, bacteria such as the genus *Escherichia*, cyanobacteria, yeasts such as the genus *Saccharomyces*, algae or protozoa such as dinoflagellates such as Crypthecodinium. Preferred organisms are those naturally able to synthesize oils in large quantities, such as microorganisms such as fungi such as *Mortierella alpina, Pythium insidiosum* or plants such as soybean, oilseed rape, coconut, oil palm, safflower, *ricinus, calendula*, peanut, cocoa bean or sunflower or yeasts such as *Saccharomyces cerevisiae*, particularly preferably soybean, oilseed rape, sunflower, *Carthamus* or *Saccharomyces cerevisiae*.

The organisms used in the processes are grown or cultured in a manner known to the skilled worker depending on the host organism. Microorganisms are usually grown in a liquid medium which comprises a source of carbon, usually in the form of sugars, a source of nitrogen, usually in the form of organic sources of nitrogen, such as yeast extract or salts such as ammonium sulfate, trace elements such as salts of iron, manganese and magnesium and, where appropriate, vitamins, at temperatures between 0° C. and 100° C., preferably between 10° C. to 60° C., while passing in oxygen. It is possible in these cases for the pH of the nutrient fluid to be kept at a fixed value, i.e. controlled during the culturing, or not. Culturing can take place batchwise, semibatchwise or continuously. Nutrients can be introduced at the start of the fermentation or subsequently fed in semicontinuously or continuously.

Plants are, after transformation, initially regenerated as described above and then cultured or grown as usual.

After the organisms have grown, the lipids are obtained in the usual way. This is done by the organisms after harvesting being initially disrupted or used directly. The lipids are advantageously extracted with suitable solvents such as apolar solvents such as hexane or ethanol, isopropanol or mixtures such as hexane/isopropanol, phenol/chloroform/isoamyl alcohol at temperatures between 0° C. to 80° C., preferably between 20° C. to 50° C. The biomass is ordinarily extracted with an excess of solvent, for example an excess of solvent to biomass of 1:4. The solvent is then removed for example by distillation. The extraction can also take place with supercritical $CO_2$. The biomass remaining after extraction can be removed for example by filtration.

The crude oil obtained in this way can then be purified further, for example by removing suspended matter by mixing with polar solvents such as acetone or chloroform and subsequent filtration or centrifugation. Further purification on columns is also possible.

Free fatty acids are obtained from the triglycerides by hydrolysis thereof in a usual way.

The invention further relates to unsaturated fatty acids, and triglycerides having an increased content of unsaturated fatty acids, which have been produced by the abovementioned processes, and to the use thereof for producing human foods, animal feed, cosmetics or pharmaceuticals. For this purpose they are added to the human foods, the animal feed, the cosmetics or pharmaceuticals in the usual quantities.

The invention is explained further by the following examples:

EXAMPLES

Example 1

General Cloning Methods

The cloning methods such as, for example, restriction cleavages, agarose gel electrophoresis, purification of DNA fragments, transfer of nucleic acids to nitrocellulose and nylon membranes, linkage of DNA fragments, transformation of *Escherichia coli* cells, culturing of bacteria and sequence analysis of recombinant DNA were carried out as described in Sambrook et al. (1989) (Cold Spring Harbor Laboratory Press: ISBN 0-87969-309-6).

Example 2

Sequence Analysis of Recombinant DNA

Recombinant DNA molecules were sequenced using an ABI laser fluorescence DNA sequencer by the method of Sanger (Sanger et al. (1977) Proc. Natl. Acad. Sci. USA74, 5463-5467). Fragments resulting from a polymerase chain reaction were sequenced and checked to avoid polymerase errors in constructs to be expressed.

Example 3

Cloning of the Δ-4-Desaturase from *Euglena gracilis*

*Euglena gracilis* strain 1224-5/25 was obtained from the Sammlung für Algenkulturen Göttingen (SAG). For isolation, the strain was grown in medium II (Calvayrac R and Douce R, FEBS Letters 7:259-262, 1970) at 23° C. with a light/dark interval of 8 h/16 h (light intensity 35 mol s-1 m-2) for 4 days.

Total RNA was isolated from a four-day *Euglena* culture with the aid of the RNAeasy kit from Qiagen (Valencia, Calif., US). Poly-A+ RNA (mRNA) was isolated from the total RNA with the aid of oligo-dT-cellulose (Sambrook et al., 1989). The reverse transcription system kit from Promega was used for reverse transcription of the RNA, and the synthesized cDNA was cloned into the lambda ZAP vector (lambda ZAP Gold, Stratagene). The cDNA was depackaged in accordance with the manufacturer's instructions to give the plasmid DNA, and clones were partially sequenced for the random sequencing. One sequence showed similarity to Δ-4-desaturases. The sequence found was used as probe for screening the phage cDNA (2*10$^5$ plaques). After two rounds of screening it was possible to identify a cDNA with full-length sequence.

Example 4

Cloning of Expression Plasmids for Heterologous Expression in Yeasts

The cloned cDNA comprises two putative start codons which result in two open reading frames with a difference of 9 bases. Only the shorter reading frame (SEQ ID NO: 1) showed activity later. The following primer pair was used in order to clone this reading frame into the vector pYES2 (Invitrogen):

```
Forward: 5'-GGTACCATGTTGGTGCTGTTTGGCAA
         (SEQ ID NO: 3)

Reverse: 5'-CTCGAGTTATGACTTTTTGTCCCCG
         (SEQ ID NO: 4)
```

Composition of the PCR mixture (50 µL):

5.00 µL Template cDNA 5.00 µL 10× buffer (Advantage polymerase)+25 mM MgCl$_2$ 5.00 µL 2 mM dNTP 1.25 µL each primer (10 pmol/µL)

0.50 µL Advantage polymerase

The Advantage polymerase from Clontech was employed.

PCR reaction conditions:

Annealing temperature: 1 min 55° C.

Denaturation temperature: 1 min 94° C.

Elongation temperature: 2 min 72° C.

Number of cycles: 35

The PCR product was incubated with the restriction enzymes KpnI and XhoI at 37° C. for 2 h. The yeast expression vector pYES2 was incubated in the same way. The PCR product 1638 bp in size, and the vector were then fractionated by agarose gel electrophoresis, and the corresponding DNA fragments were cut out. The DNA was purified using a Qiagen gel purification kit in accordance with the manufacturer's instructions. Vector and Δ-4-desaturase cDNA were then ligated. The rapid ligation kit from Roche was used for this purpose. The resulting plasmid pYES2-EGD4-2 was verified by sequencing and transformed into the *saccharomyces* strain SC334 by electroporation (1500 V). The yeasts were then plated out on minimal medium without uracil. Cells able to grow on minimal medium without uracil thus comprise the plasmid pYES2-EGD4-2.

Example 5

Cloning of Expression Plasmids for Seed-Specific Expression in Plants

A further transformation vector based on pSUN-USP was generated for the transformation of plants. For this purpose, NotI cleavage sites were introduced at the 5' and 3' end of the coding sequence using the following primer pair:

```
Forward: 5'-GCGGCCGCATGTTGGTGCTGTTTGGCAA
         (SEQ ID NO: 5)

Reverse: 5'-GCGGCCGCATGACTTTTTGTCCCCG
         (SEQ ID NO: 6)
```

Composition of the PCR mixture (50 µL):

5.00 µL Template cDNA 5.00 µL 10× buffer (Advantage polymerase)+25 mM MgCl$_2$ 5.00 µL 2 mM dNTP 1.25 µL each primer (10 pmol/µL)

0.50 µL Advantage polymerase

The Advantage polymerase from Clontech was employed.

PCR reaction conditions:

Annealing temperature: 1 min 55° C.

Denaturation temperature: 1 min 94° C.

Elongation temperature: 2 min 72° C.

Number of cycles: 35

The PCR product was incubated with the restriction enzyme NotI at 37° C. for 16 h. The plant expression vector pSUN300-USP was incubated in the same way. The PCR product 1642 bp in size, and the vector 7624 bp in size, were then fractionated by agarose gel electrophoresis, and the corresponding DNA fragments were cut out. The DNA was purified using a Qiagen gel purification kit in accordance with the manufacturer's instructions. Vector and Δ-4-desaturase cDNA were then ligated. The rapid ligation kit from Roche was used for this purpose. The resulting plasmid pSUN-EGD4-2 was verified by sequencing.

pSUN300 is a derivative of the plasmid pPZP (Hajdukiewicz, P, Svab, Z, Maliga, P., (1994) The small versatile pPZP family of *Agrobacterium* binary vectors for plant transformation. Plant Mol Biol 25:989-994). pSUN-USP was produced from pSUN300 by inserting a USP promoter as EcoRI fragment into pSUN300. The polyadenylation signal is that of the octopine synthase gene from the *A. tumefaciens* Ti plasmid (ocs terminator, Genbank Accession V00088) (De Greve, H., Dhaese, P., Seurinck, J., Lemmers, M., Van Montagu, M. and Schell, J. Nucleotide sequence and transcript map of the *Agrobacterium tumefaciens* Ti plasmid-encoded octopine synthase gene J. Mol. Appl. Genet. 1 (6), 499-511 (1982) The USP promoter corresponds to nucleotides 1 684 (Genbank Accession X56240), with part of the non-coding region of the USP gene being present in the promoter. The promoter fragment which is 684 base pairs in size was amplified by a PCR reaction using commercially available T7 standard primers (Stratagene) and with the aid of a synthesized primer by standard methods (primer sequence: 5'-GTCGACCCGCG-GACTAGTGGGCCCTCTAGACCCGGGGGATCC GGATCTGCTGGCTATGAA-3', SEQ ID NO: 7). The PCR fragment was then cut with EcoRI/SalI and inserted into the vector pSUN300 with OCS terminator. The result was the plasmid called pSUN-USP. The construct was used to transform *Arabidopsis thaliana*, oilseed rape, tobacco and linseed.

Example 6

Generation of Transgenic Plants a) Generation of transgenic oilseed rape plants (modification of Moloney et al., 1992, Plant Cell Reports, 8:238-242)

Transgenic oilseed rape plants were generated by using binary vectors in *Agrobacterium tumefaciens* C58C1: pGV2260 or *Escherichia coli* (Deblaere et al, 1984, Nucl. Acids. Res. 13, 4777-4788). To transform oilseed rape plants (Var. Drakkar, NPZ Norddeutsche Planzenzucht, Hohenlieth, Germany), a 1:50 dilution of an overnight culture of a positively transformed agrobacterial colony in Murashige-Skoog medium (Murashige and Skoog 1962 Physiol. Plant. 15, 473) with 3% sucrose (3MS medium) was used. Petiols or hypocotyls of freshly germinated sterile oilseed rape plants (each about 1 cm²) were incubated with a 1:50 agrobacterial dilution in a Petri dish for 5-10 minutes. This was followed by coincubation on 3MS medium with 0.8% Bacto agar at 25° C. in the dark for 3 days.

The cultivation was continued after 3 days with 16 hours of light/8 hours of dark and continued in a weekly rhythm on MS medium with 500 mg/l Claforan (cefotaxime sodium), 50 mg/l canamycin, 20 microM benzylaminopurine (BAP) and 1.6 g/l glucose. Growing shoots were transferred to MS medium with 2% sucrose, 250 mg/l Claforan and 0.8% Bacto agar. If no roots formed after three weeks, 2-indolebutyric acid was added as growth hormone to the medium for rooting.

Regenerated shoots are maintained on. 2MS medium with canamycin and Claforan, transferred into soil after rooting and, after cultivation for two weeks, grown in a controlled-enviroment cabinet or in a greenhouse and allowed to flower, and ripe seeds are harvested and investigated for Δ-4-desaturase expression by lipid analyses. Lines with increased contents of or double bonds at the Δ-4 position are identified. An increased content of double bonds at the Δ-4 position compared with untransformed control plants can be found in the stably transformed transgenic lines which functionally express the transgene.

b) Transgenic linseed plants can be produced for example by the method of Bell et al., 1999, In Vitro Cell. Dev. Biol.-Plant. 35(6):456-465 by means of particle bombardment. *Agrobacteria*-mediated transformations can be produced for example by the method of Mlynarova et al. (1994), Plant Cell Report 13: 282-285.

Example 7

Lipid Extraction from Yeasts

Yeasts transformed with the plasmid pYES-EGD4-2 as in Example 4 were analyzed in the following way:

The yeast cells were grown in 1 ml of minimal medium with 0.2% raffinose for two days and then transferred into 5 ml of the same medium. This culture was grown at 30° C. for 6 h until the OD600 was 0.05. Then 100 µM of the fatty acid substrates (67 µM for 16:1 Δ7) were added, and the expression of the Δ-4-desaturase was induced by adding 2% galactose. The cells were then incubated at 15° C. for 4 days, harvested, washed with 100 mM NaHCO3 and employed for the fatty acid analysis by GC.

FIG. 4 shows the result of the fatty acid analysis. It was possible to show in this case that, compared with the control yeast strain which does not have the Δ-4-desaturase gene, the fatty acid DPA (docosapentaenoic acid) which was fed was desaturated to DHA (docosahexaenoic acid) in the yeast strain with the pYES-EGD4-2 construct.

The substrate specificities were found by feeding the transformed yeast strains with different fatty acids (Tab. 1). Conversion of the fed fatty acids to their Δ4-desaturated products was then determined.

The method is described for example in Napier and Michaelson, 2001, Lipids. 36(8):761-766; Sayanova et al., 2001, Journal of Experimental Botany. 52(360):1581-1585, Sperling et al., 2001, Arch. Biochem. Biophys. 388(2):293-298 and Michaelson et al., 1998, FEBS Letters. 439(3):215-218.

Analysis of the substrate specificity showed that the C7-C8 double bond is necessary for substrate recognition.

TABLE 1

Substrate specificity of the *Euglena gracilis* Δ4-desaturase

| Fatty acid fed | Conversion (in %) |
| --- | --- |
| 22:5 Δ7, 10, 13, 16, 19 | 29.7 (±2.8) |
| 22:4 Δ7, 10, 13, 16 | 28.7 (±2.5) |
| 20:3 Δ8, 11, 14 | Not detectable |
| 18:3 Δ6, 9, 12 | Not detectable |
| 18:2 Δ9, 12 | Not detectable |
| 18:1 Δ9 | Not detectable |
| 18:0 | Not detectable |
| 16:3 Δ7, 10, 13 | 21.4 (±3.3) |
| 16:1 Δ7 | 7.4 (±0.8) |
| 16:1 Δ9 | Not detectable |
| 16:0 | Not detectable |

Example 8

Position Analysis of the Δ4-Desaturated Fatty Acids

Besides the substrate specificity, the position of the Δ-4-desaturated fatty acids was also analyzed. The position of polyunsaturated fatty acids is important from the view points of nutritional physiology. It has been reported that unsaturated fatty acids particularly in the sn-2 position of triacylglycerides are rapidly absorbed in the intestine of mammals. The procedure for investigating the positional specificity of the Δ-4-desaturase from *Euglena gracilis* was as follows:

As described in Example 4, 100 ml of yeast culture which express the Δ-4-desaturase from yeast were fed with 16:1 Δ7 and with 22:4 Δ7, 10, 13, 16 and then incubated. The total lipids were isolated from the yeasts by chloroform/methanol/water extraction (Bligh, E. G. and Dyer, W. J. Can J Biochem Physiol 37:911-917, 1959) and fractionated by thin layer chromatography (chloroform/methanol/acetic acid 65:25:8). Phosphatidylcholine were scraped off the thin layer plates and extracted with 2 ml of chloroform/methanol (2/1). The extracted phosphatidylcholine was dried and resuspended in 50 µL of 100% Triton-100. 1 ml of 50 mM HEPES, 2 mM $CaCl_2$ and 10 000 units of lipase (*Rhizopus arrhizus delemar*, Sigma) was added to the solution. After incubation at 37° C. for 2 hours, the solution was acidified with acetic acid (100%), and the lipids and free fatty acids were extracted with chloroform/methanol. The free fatty acids and the resulting lysophosphatidylcholine were separated by thin layer chromatography, scraped off the plate and analyzed by GC.

The results are depicted in. FIG. 5. It is evident from this that the sn-2 position is preferred by a factor of 20 over the sn-1 position. It was thus possible to show that desaturation of the C4-C5 position takes place for the most part on fatty acids in the sn-2 position.

Example 9

Lipid Extraction from Yeasts and Seeds

The effect of the genetic modification in plants, fungi, algae, ciliates or on the production of a desired compound (such as a fatty acid) can be determined by culturing the modified microorganisms or the modified plant under suitable conditions (such as those described above) and investigating the medium and/or the cellular components for the increased production of the desired product (i.e. of lipids or of a fatty acid). These analytical techniques are known to the skilled worker and comprise spectroscopy, thin layer chromatography, staining methods of various types, enzymatic and microbiological methods, and analytical chromatography such as high performance liquid chromatography (see, for example, Ullman, Encyclopedia of Industrial Chemistry, Vol. A2, pp: 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

Besides the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the final product of the fermentation, it is also possible to analyze other components of the metabolic pathways used to produce the desired compound, such as intermediates and byproducts, in order to determine the overall efficiency of production of the compound. The analytical methods comprise measurements of the amounts of nutrients in the medium (e.g. sugars, hydrocarbons, sources of nitrogen, phosphate and other ions), measurements of the biomass composition and of growth, analysis of the production of usual metabolites of biosynthetic pathways and measurements of gases produced during the fermentation. Standard methods for these measurements are described in Applied Microbial Physiology; A Practical Approach, P. M. Rhodes and P. F. Stanbury, Editors, IRL Press, pp. 103-129; 131-163 and 165-192 (ISBN: 0199635773) and references cited therein.

One example is analysis of fatty acids (abbreviations: FAME, fatty acid methyl esters; GC-MS, gas-liquid chromatography-mass spectrometry; TAG, triacylglycerol; TLC, thin layer chromatography).

Unambiguous detection of the presence of fatty acid products is possible by analyzing recombinant organisms by standard analytical methods: GC, GC-MS or TLC as variously described by Christie and the references therein (1997, in: Advances on Lipid Methodology, Fourth edition: Christie, Oily Press, Dundee, 119-169; 1998, Gas chromatography-mass spectrometry methods, Lipide 33:343-353).

The material to be analyzed can be disrupted by ultrasound treatment, grinding in a glass mill, liquid nitrogen and grinding or by other applicable methods. The material must be centrifuged after the disruption. The sediment is resuspended in distilled water, heated at 100° C. for 10 min, cooled on ice and again centrifuged, followed by extraction in 0.5 M sulfuric acid in methanol with 2% dimethoxypropane at 90° C. for 1 h, leading to hydrolyzed oil and lipid compounds which afford transmethylated lipids. These fatty acid methyl esters are extracted into petroleum ether and finally subjected to a GC analysis using a capillary column (Chrompack, WCOT Fused Silica, CP-Wax-52 CB, 25 microm, 0.32 mm) with a temperature gradient between 170° C. and 240° C. for 20 min and 5 min at 240° C. The identity of the resulting fatty acid methyl esters must be defined by use of standards which are obtainable from commercial sources (i.e. Sigma).

Plant material is initially homogenized mechanically by grinding in a mortar in order to make it more amenable to extraction.

It is then heated at 100° C. for 10 min and, after cooling on ice, again sedimented. The cell sediment is hydrolyzed, and the lipids are transmethylated, with 1 M methanolic sulfuric acid and 2% dimethoxypropane at 90° C. for 1 h. The resulting fatty acid methyl esters (FAME) are extracted into petroleum ether. The extracted FAME are analyzed by gas-liquid chromatography using a capillary column (Chrompack, WCOT Fused Silica, CP-Wax-52 CB, 25 m, 0.32 mm) and a temperature gradient from 170° C. to 240° C. in 20 min and 5 min at 240° C. The identity of the fatty acid methyl esters is confirmed by comparison with appropriate FAME standards (Sigma). The identity and the position of the double bond can be analyzed further by suitable chemical derivatization of the FAME mixtures, e.g. to give 4,4-dimethoxyoxazoline derivatives (Christie, 1998) by means of GC-MS.

---

We claim:

1. An isolated nucleic acid comprising a nucleotide sequence selected from the group consisting of:
   a) the nucleotide sequence as depicted in SEQ ID NO: 1,
   b) a nucleotide sequence which codes for a polypeptide having the amino acid sequence of SEQ ID NO: 2, and
   c) a nucleotide sequence which codes for a polypeptide having at least 95% homology at the amino acid level with SEQ ID NO: 2, wherein the polypeptide has Δ-4-desaturase activity.

2. The isolated nucleic acid of claim 1, wherein the sequence is derived from a plant.

3. The isolated nucleic acid of claim 1, wherein the sequence is derived from the class of Euglenophyceae.

4. A gene construct comprising the isolated nucleic acid of claim 1, wherein the nucleic acid is functionally connected to one or more regulatory signals.

5. The gene construct of claim 4, wherein the gene construct comprises additional biosynthesis genes of fatty acid or lipid metabolism selected from the group consisting of acyl-CoA dehydrogenase(s), acyl-ACP [=acyl carrier protein] desaturase(s), acyl-ACP thioesterase(s), fat acid acyltransferase(s), acyl-CoA:lysophospholipid acyltransferase(s), fatty acid synthase(s), fatty acid hydroxylase(s), acetyl-coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases, and fatty acid elongase(s).

6. The gene construct of claim 4, wherein the gene construct comprises additional biosynthesis genes of fatty acid or lipid metabolism selected from the group consisting of Δ-4-desaturase, Δ-5-desaturase, Δ-6-desaturase, Δ-8-desaturase, Δ-9-desaturase, Δ-12-desaturase, Δ-5-elongase, Δ-6-elongase, and Δ-9-elongase.

7. A vector comprising the nucleic acid of claim 1.

8. A transgenic nonhuman organism comprising at least one nucleic acid of claim 1, wherein the nonhuman organism is a microorganism, a yeast, or a plant.

9. The transgenic nonhuman organism of claim 8, wherein the organism is a plant.

10. A process for producing polyunsaturated fatty acids, comprising growing a transgenic organism which comprises the nucleic acid of claim 1, producing polyunsaturated fatty acids in said organism, and recovering the polyunsaturated fatty acids, wherein the organism is a yeast or a plant.

11. The process of claim 10, wherein docosahexaenoic acid is produced in the process.

12. The process of claim 10, wherein the polyunsaturated fatty acids are isolated from the organism in the form of an oil, lipid or a free fatty acid.

13. The process of claim 10, wherein the organism is a transgenic plant.

* * * * *

UNITED STATES PATENT AND TRADEMARK OFFICE
CERTIFICATE OF CORRECTION

PATENT NO. : 7,629,503 B2 Page 1 of 1
APPLICATION NO. : 10/552127
DATED : December 8, 2009
INVENTOR(S) : Cirpus et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 632 days.

Signed and Sealed this

Second Day of November, 2010

David J. Kappos
*Director of the United States Patent and Trademark Office*